United States Patent [19]
Axe et al.

[11] Patent Number: 5,458,137
[45] Date of Patent: Oct. 17, 1995

[54] METHOD AND APPARATUS FOR CONTROLLING SLEEP DISORDER BREATHING

[75] Inventors: John R. Axe; Khosrow Bebehani, both of Arlington; John R. Burk, Aledo; Edgar A. Lucas, Fort Worth; Fu-Chung Yen, Arlington, all of Tex.

[73] Assignee: Respironics, Inc., Murrysville, Pa.

[21] Appl. No.: 47,826

[22] Filed: Apr. 15, 1993

Related U.S. Application Data

[63] Continuation-in-part of Ser. No. 715,374, Jun. 14, 1991, Pat. No. 5,203,343.

[51] Int. Cl.$^6$ .......................... A61M 16/00; A62B 7/00; F16K 31/02
[52] U.S. Cl. .................. 128/204.23; 128/204.21
[58] Field of Search .......... 128/204.18, 204.21, 128/204.23, 202.22, 202.27

[56] References Cited

U.S. PATENT DOCUMENTS

| | | | |
|---|---|---|---|
| 3,882,847 | 5/1975 | Jacobs. | |
| 4,648,407 | 3/1987 | Sackner | 128/204.23 |
| 4,766,894 | 8/1988 | Legrand et al. | 128/202.22 |
| 4,782,832 | 11/1988 | Trimble et al. | 128/207.18 |
| 4,803,471 | 2/1989 | Rowland | 128/202.22 |
| 4,825,802 | 5/1989 | Le Bec | 128/202.22 |
| 4,860,766 | 8/1989 | Sackner | 128/204.23 |
| 4,919,128 | 4/1990 | Kopala et al. | 128/207.18 |
| 4,944,310 | 7/1990 | Sullivan | 128/848 |
| 4,972,842 | 11/1990 | Korten et al. | 128/204.23 |
| 5,107,831 | 4/1992 | Halpern et al. | 128/204.23 |
| 5,117,819 | 6/1992 | Servidio et al. | 128/204.18 |
| 5,134,995 | 8/1992 | Gruenke et al. | 128/204.23 |
| 5,148,802 | 9/1992 | Sanders et al. | 128/204.18 |
| 5,161,525 | 11/1992 | Kimm et al. | 128/204.23 |
| 5,165,397 | 11/1992 | Arp | 128/204.23 |
| 5,203,343 | 4/1993 | Axe et al. | 128/204.23 |
| 5,239,995 | 8/1993 | Estes et al. | 128/204.23 |
| 5,245,995 | 9/1993 | Sullivan et al. | 128/205.25 |
| 5,259,373 | 11/1993 | Gruenke et al. | 128/205.25 |
| 5,313,937 | 5/1994 | Zdrojkowski et al. | 128/205.23 |

FOREIGN PATENT DOCUMENTS

| | | | |
|---|---|---|---|
| WO88/10108 | 12/1988 | WIPO | 128/204.23 |
| WO89/10768 | 11/1989 | WIPO | 128/204.21 |
| WO90/14121 | 11/1990 | WIPO | 128/204.23 |

Primary Examiner—Kimberly L. Asher

[57] ABSTRACT

A method and device for controlling sleep disorder breathing utilizes variable multiple level pressures. A pressure source supplies compressed breathable gas at a relatively low pressure to the user's airway. Pressure transducers monitor pressures and convert them into electrical signals. The electrical signals are filtered and processed to extract specific features such as duration and energy levels. If these features exceed selected threshold values for duration and energy level over a minimum period of time, then the microprocessor declares the presence of sleep disorder breathing. If a selected number of these events occur within a selected time period, then the microprocessor adjusts the pressure delivered by the pressure source. If sleep disorder breathing is not detected within a certain time period, then the microprocessor lowers the pressure level gradually. The device and method disclosed in this patent is capable of detecting apnea, hypopnea, and pharyngeal wall vibration. Further, it is able to distinguish between obstructive, central and mixed apnea and hypopnea.

43 Claims, 19 Drawing Sheets

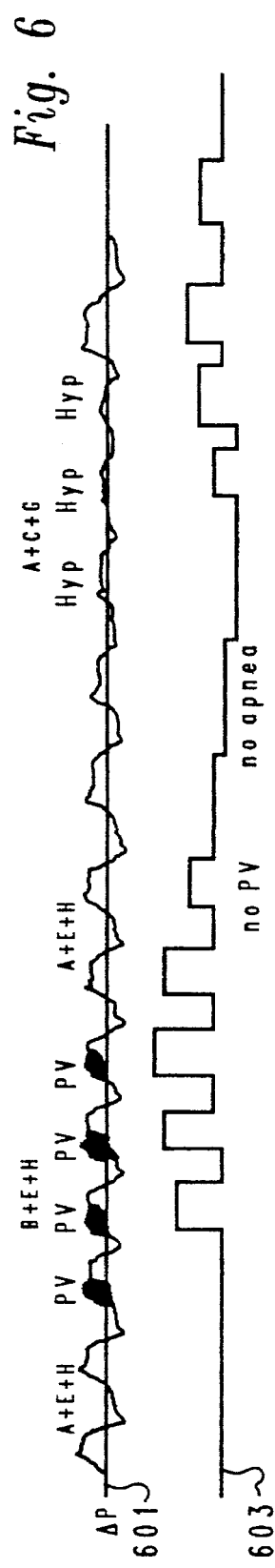
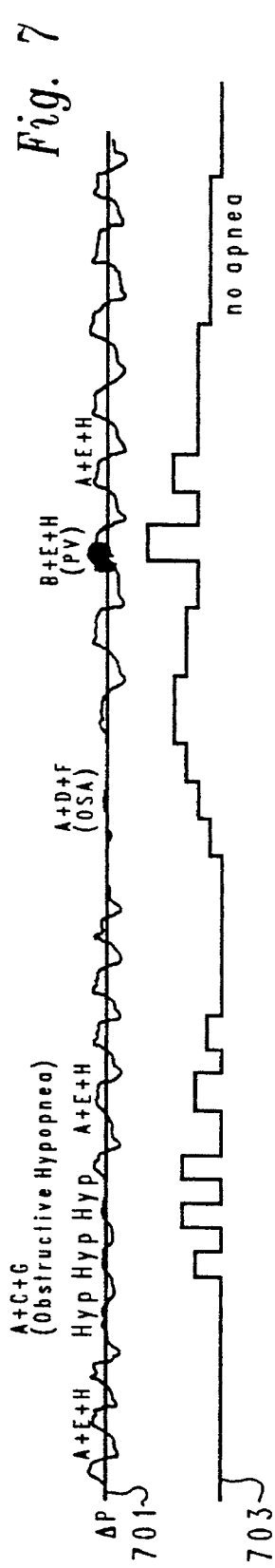
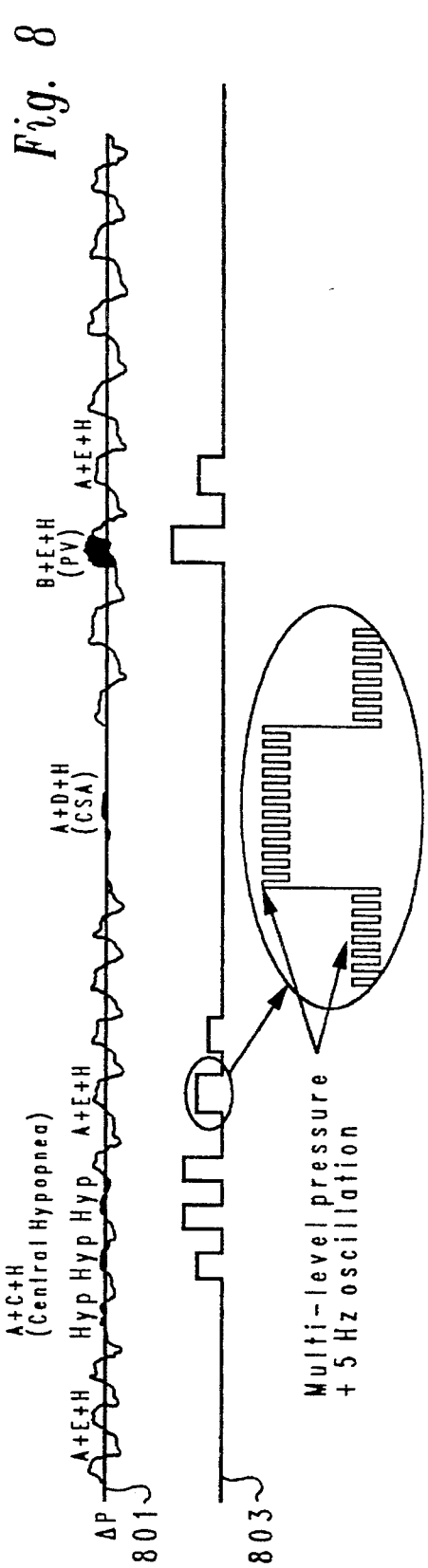

METHOD AND APPARATUS FOR CONTROLLING SLEEP DISORDER BREATHING

CROSS REFERENCE TO RELATED APPLICATION

This application is a continuation-in-part of application Ser. No. 07/715,374, filed Jun. 14, 1991, John R. Axe, et al. now U.S. Pat. No. 5,203,343.

BACKGROUND OF THE INVENTION

1. Field of the Invention

This invention relates in general to a method and apparatus for controlling sleep disorder breathing, particularly one utilizing positive air pressure supplied to a person's breathing passages.

2. Description of the Prior Art

The majority of patients diagnosed with sleep disorders in the United States suffer from excessive daytime sleepiness. The leading cause of this symptom is sleep apnea.

Sleep disorder breathing, such as hypopnea, apnea, or other partial pharyngeal closure, is often combined with pharyngeal wall vibration, which may or may not be audible. Sleep apnea is a potentially lethal condition characterized by multiple obstructive, central or mixed apneas occurring during sleep. A characteristic symptom of sleep apnea includes repetitive episodes of pharyngeal wall vibration, often referred to as snoring when audible. The vibration noted with this syndrome is one in which inspiratory vibrations gradually increase when pharyngeal closure or obstruction of the upper airway develops. A loud, choking inspiratory gasp then occurs as a person's respiratory efforts succeed in overcoming the occlusion. The person frequently wakes. In the morning, the aroused person is usually aware of neither the breathing difficulty nor of the numerous accompanying body movements that at times violently disturb his sleep. A diagnostic study is necessary for an adequate description of the person's sleep breathing pattern.

Apneic episodes during sleep are defined as cessations of air flow at nose and mouth lasting 10 seconds or longer and can be readily documented by polysomnographic recordings. Variations in night-to-night frequency of apneic pauses exist in many patients, with increased frequency appearing to follow upper respiratory infections or use of sedating drugs or alcohol.

In obstructive sleep apnea (OSA), breathing passageways are blocked. In central sleep apnea (CSA), the brain has ceased signaling the body to breathe. Obstructive hypopnea is a milder form of obstructive apnea, usually referring to episodes of partial obstruction of the upper airway passages. Central hypopnea is a milder form of central apnea. Excessive pharyngeal wall vibration, without hypopnea or apnea occurrences, can also be a serious problem. Obstructive and central apnea, obstructive and central hypopnea, and pharyngeal wall vibration will be referred to herein as sleep disorder breathing. In the case of central apnea, the passageways are still open. The lungs of the person form a reservoir for air flow even though the person is not breathing.

Treatments available for sleep apnea vary from weight loss to surgical intervention to prosthetic devices. Although weight loss is the most desirable approach, few patients are able to comply with their diets, and very few can afford to continue the exposure to the symptoms of sleep apnea for six months to a year while losing sufficient weight to reduce or cure the condition. Surgical approaches are only effective in about 50% of the cases, are invasive, expensive and may produce undesirable side effects.

The most successful treatment device has been the nasal continuous positive airway ventilator ("CCPAP"). CPAP initially used an adapted vacuum sweeper motor to supply air under pressure to a hose. The hose fed a nasal mask attached it to the patient's face. The advantages of the nasal CPAP system are that it produces immediate relief, is non-invasive and can be used while achieving weight loss and thus avoids the need for surgery. The primary problem with nasal CPAP has been compliance. While nearly all of patients are fitted with nasal-CPAP as an initial treatment modality, many cease using the system after about six months.

Investigation of the causes for poor compliance among patients has identified three primary factors all relating to patient comfort. The first factor is the lack of perfect fit and discomfort of wearing the nasal mask. The positive pressure of the ventilator flow is often mentioned as the second factor. Some patients experience an uncomfortable and annoying sensation from the forced air stream in their nose and mount. Third, dry mouth and throat are often cited as the source of dissatisfaction with the sleep apnea ventilators.

SUMMARY OF THE INVENTION

The method and apparatus of the invention provide for the detection and control of sleep disorder breathing in a person. Control of sleep disorder breathing with reduced discomfort due to flow of forced air, is accomplished by selection of pressure for the air flow. Increased pressure is selected upon detection of sleep disorder breathing. Absent occurrence of sleep disorder breathing, the forced air flow is reduced in pressure.

For sleep, a patient is fitted with a nasal mask adapted to deliver air from a source of compressed air to the patient's nasal passages. A hose connects the compressed air source and nasal mask. Detection of sleep disorder breathing involves monitoring of face mask pressure and pressure difference (ΔP) between two spaced points along the hose. Specific conditions, including occurrence of apnea, hypopnea and pharyngeal wall vibration are identified. Also detectable are nasal mask problems such as dislodgement of the mask or leakage from the mask. Inhalation and exhalation by the patient are also detected. Diagnosis of apnea, hypopnea, pharyngeal wall vibration and complete or partial closure of the breathing path is based on measurements of breathing by the patient.

Pressure selection is microprocessor controlled and is responsive to detection of specific conditions. Pressure may be adjusted to multiple levels during and following occurrences of sleep disorder breathing. Increased pressure for inhalation, exhalation, or both may be used to suppress sleep disorder breathing, with the pressure level adjusted to achieve suppression of the condition. Mask dislodgement results in reduction of pressure to a minimum level.

BRIEF DESCRIPTION OF THE DRAWINGS

FIG. 6 is a pair of graphs, one illustrating the difference in pressure that exists between the mask and the compressor output and the other illustrating command pressure to the compressor for periods of normal breathing as well as episodes of pharyngeal wall vibration and obstructive hypopnea;

FIG. 7 is a pair of graphs, one illustrating the difference in pressure that exists between the mask and the compressor output and the other illustrating command pressure to the compressor for normal breathing as well as episodes of pharyngeal wall vibration, obstructive hypopnea, and obstructive apnea;

FIG. 8 is a pair of graphs, one illustrating the difference in pressure that exists between the mask and the compressor output and the other illustrating command pressure to the compressor for normal breathing as well as episodes of central hypopnea, and central apnea; and FIGS. 9–29 are logical flow charts of a computer process executed on a microprocessor detecting episodes of control and obstructive hypopnea and adjusting mask pressure for the control thereof.

DETAILED DESCRIPTION OF THE INVENTION

Figure 1:
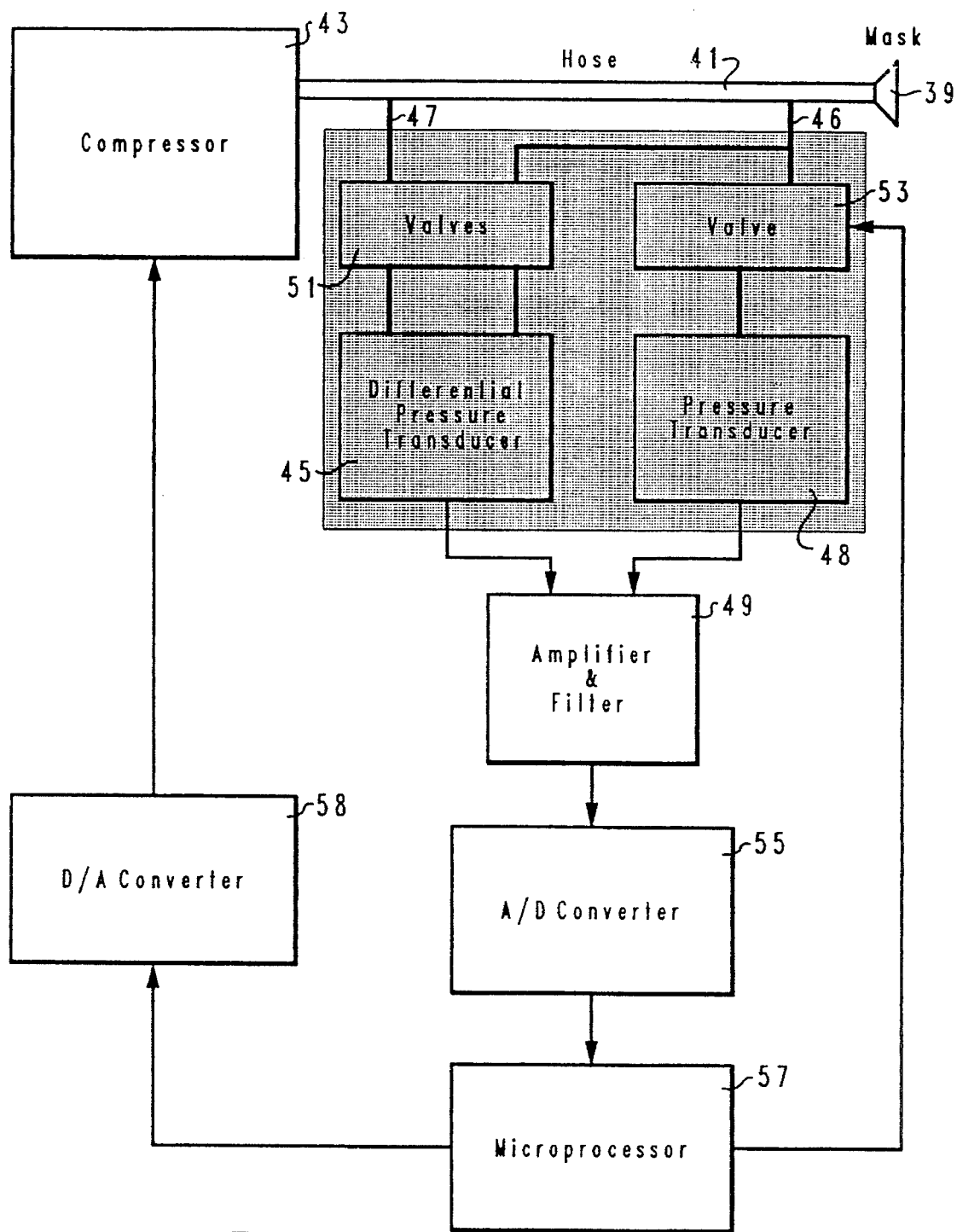
FIG. 1 is a block diagram illustrating the method and apparatus of this invention.

Referring to FIG. 1, the apparatus will include any type of mask or nostril adapter 39. Mask 39 may be a commercially available product that has two nozzles, each of which fits within a nostril (not shown) of a user. Mask 39 connects to a flexible hose 41 that leads to a low pressure air source such as compressor 43. Mask 39 and hose 41 make up an interface for supplying air under pressure to the user. Compressor 43 draws in ambient air and compresses it to a pressure which can be selected as described below. Increasing the pressure will increase the flow rate of the air through the hose 41 if mask 39 is open to atmosphere.

The differential pressure transducer 45 senses the dynamic pressure difference between the output of the compressor 43 and the mask 39. Differential pressure transducer 45 has one sensing tube 46 connected to the interior of mask 39. Another sensing tube 47 connects to the output of compressor 43. Mask sensing tube 46 is downstream from output pressure sensing tube 47. The pressure difference between sensing tubes 46 and 47 corresponds to the quantity of air flow through the hose 41. Normal breathing causes the difference in pressure sensed by the pressure transducer 45 to fluctuate.

Pressure transducer 48 measures only the dynamic pressure in the mask 39. Pressure transducer 48 is connected to sensing tube 46. Mask pressure transducer 48 and differential pressure transducer 45 apply analog signals to amplifier/filter circuitry 49. The amplifier/filter circuitry 49 amplify the signal and may optionally filter out signals clearly not associated with sleep disorder breathing. Electrically actuated valves 51, 53 connected into sensing tubes 47, 46, respectively, are normally closed. These valves are used for periodic calibration of pressure transducers 45 and 48. When actuated, each valve 51, 53 opens the sensing tubes 46, 47 to the atmosphere. The amplifier 49 applies the sensed pressure waveforms to an analog to digital converter 55, which in turn is applied to a microprocessor 57. Microprocessor 57 will control the output pressure of the pressure source 43 of the pressure transducers 45 and 48 respectively. Microprocessor 57 performs the calibration, also on a timed basis.

The microprocessor 57 is programmed to sample the incoming signals from converter 55 at a rate of 4000 times per second and process the sampled signals at the rate of 10 times per second. For every 400 pressure difference values collected, a mean pressure difference value and a pressure difference standard deviation value are calculated and stored. The mean pressure difference value calculation is, in effect, a low pass filter, whereas the standard deviation calculation is, in effect, a high pass filter. The mean pressure difference values are used to calculate a mean pressure difference base line, which is arbitrarily defined as the signal level dividing inspiration and expiration.

If the mean value is larger than the pressure difference base line value by a threshold for more than 15 seconds, the algorithm responds with a "mask off" signal. Experience has shown that if the mask 39 is removed, the pressure difference becomes very large and will exceed an pressure difference base line value established before the mask was dislodged.

The microprocessor 57 algorithm uses the pressure difference standard deviation values to calculate the energy of disturbances in the pressure difference signal greater than an arbitrarily defined threshold. The threshold level is determined according to the following formula:

$$\text{standard deviation threshold} = (\text{command pressure} - A) * B + C$$

where A, B and C are fixed empirical values that set the threshold above the level of disturbances caused by ordinary turbulence in the hose 41. Alternately, the standard deviation threshold values could be adaptive and changed based on past standard deviation values calculated for the person utilizing the mask 39. If the standard deviation value is equal to zero for 10 seconds then the system responds with a "power off" signal.

Detection of pharyngeal wall vibration is based on the energy and duration of the pressure waveforms associated with the sleep disorder breathing. The energy is calculated as the sum of pressure difference standard deviation values in excess of the standard deviation threshold divided by the pharyngeal wall vibration duration. The algorithm responds with a "pharyngeal wall vibration" signal when the energy of the standard deviation values is greater than an energy threshold, and when the duration of pharyngeal wall vibration exceeds a duration threshold. The command pressure is raised after a selected number of pharyngeal wall vibration signals, such as three, where the time between successive sleep disorder breathing signals does not exceed a selected duration, such as 20 seconds. The amount by which pressure from compressor 43 is raised is adjustable. The command pressure is reduced after any selected period, such as five minutes, in which no sleep disorder breathings occur. The amount by which pressure is reduced is adjustable.

The command pressure from microprocessor 57 is output as a digital signal, which passes through digital to analog converter 58 where it is converted to an analog signal for varying the speed, and thus the output pressure, of compressor 43. The microprocessor 57 can vary the output of compressor 43 with each inspiration and expiration cycle, increasing pressure during inspiration and decreasing pressure to a lower base level during expiration. Either level may be adjusted independently if sleep disorder breathing is detected. Also, the output of compressor 43 is modulated by a small amplitude 5 Hz signal, which is used to detect the difference between central and obstructive apnea and central and obstructive hypopnea.

Figure 2:
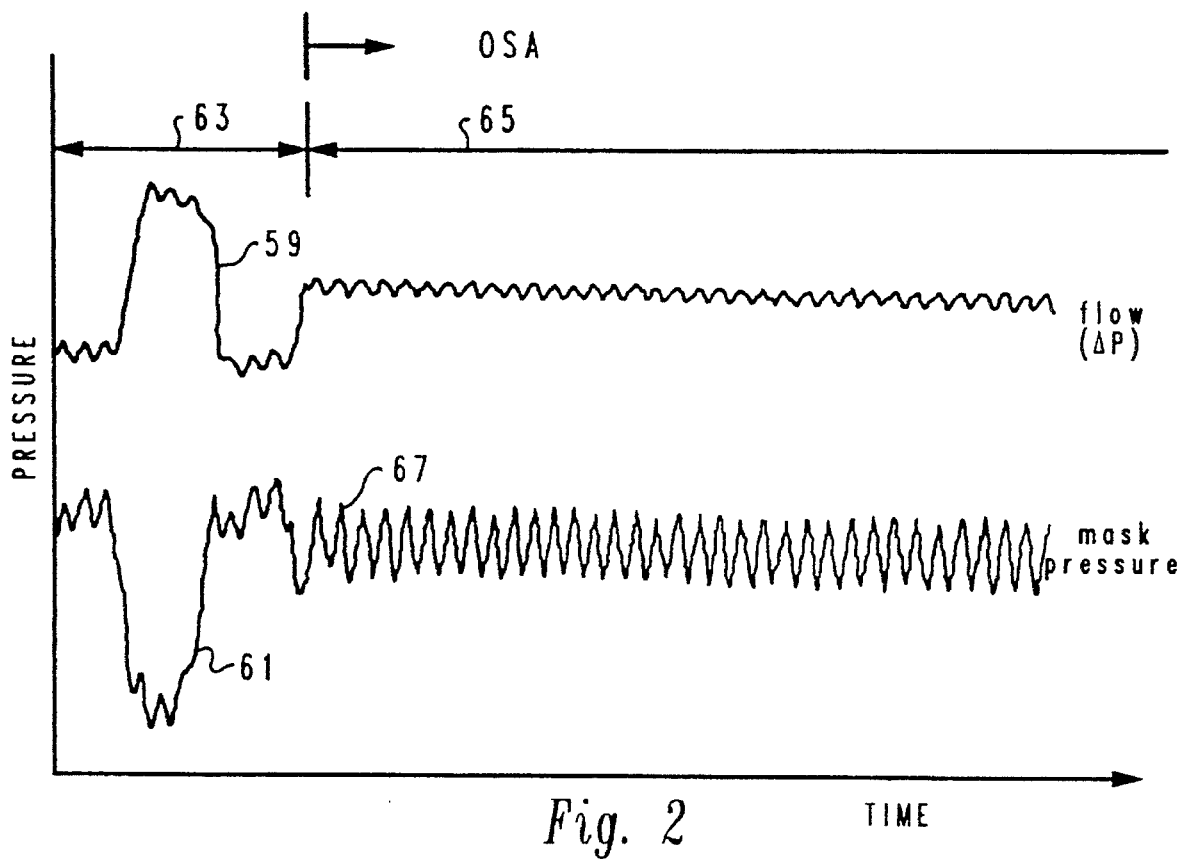
FIG. 2 is a pair of graphs, one illustrating the difference in pressure that exists between the mask and the compressor output and the other illustrating the mask pressure during an occurrence of obstructive sleep apnea.

FIGS. 2–5 illustrate graphical traces of episodes of obstructive sleep apnea (OSA), central sleep apnea (CSA), obstructive sleep hypopnea (OSH) and central sleep hypopnea (CSH), obtained from a normal subject simulating the conditions. Referring to FIG. 2, the curve 59 represents the delta P measurement measured by pressure transducer 45. Curve 61 represents the mask pressure sensed by transducer 48. The magnitudes of the pressures of curves 59 and 61, as illustrated by the graph of FIG. 2, are shown against the same time coordinate for convenience. Period 63 indicates normal breathing. During period 63, the delta P measurement 59 increases and decreases normally. The mask pressure 61 also increases and decreases normally, about 180° degrees out of phase with the delta P measurement 59, during normal breathing. Delta P 59 will be relatively high during inspiration, while the mask pressure 61 will be reduced.

Period 65 corresponds to the occurrence of OSA. During OSA, the upper airway is blocked completely. Consequently, little flow will occur and the pressure difference measurement will be insignificant. The mask pressure 61 will fluctuate as indicated by the numeral 67 proportional to the five hertz modulation applied to compressor 43 (FIG. 1).

Curve 59 is graph of a delta P measurement, or the changes in difference in pressure between sensing tubes 46, 47 over time. Under normal circumstances, delta P curve 59 is always positive with a greater pressure at compressor output sensing tube 47 than at interface sensing tube 46. The difference in pressure increases when the person inhales and decreases when the person exhales. The curve 61 represents the mask pressure during normal breathing.

Figure 3:
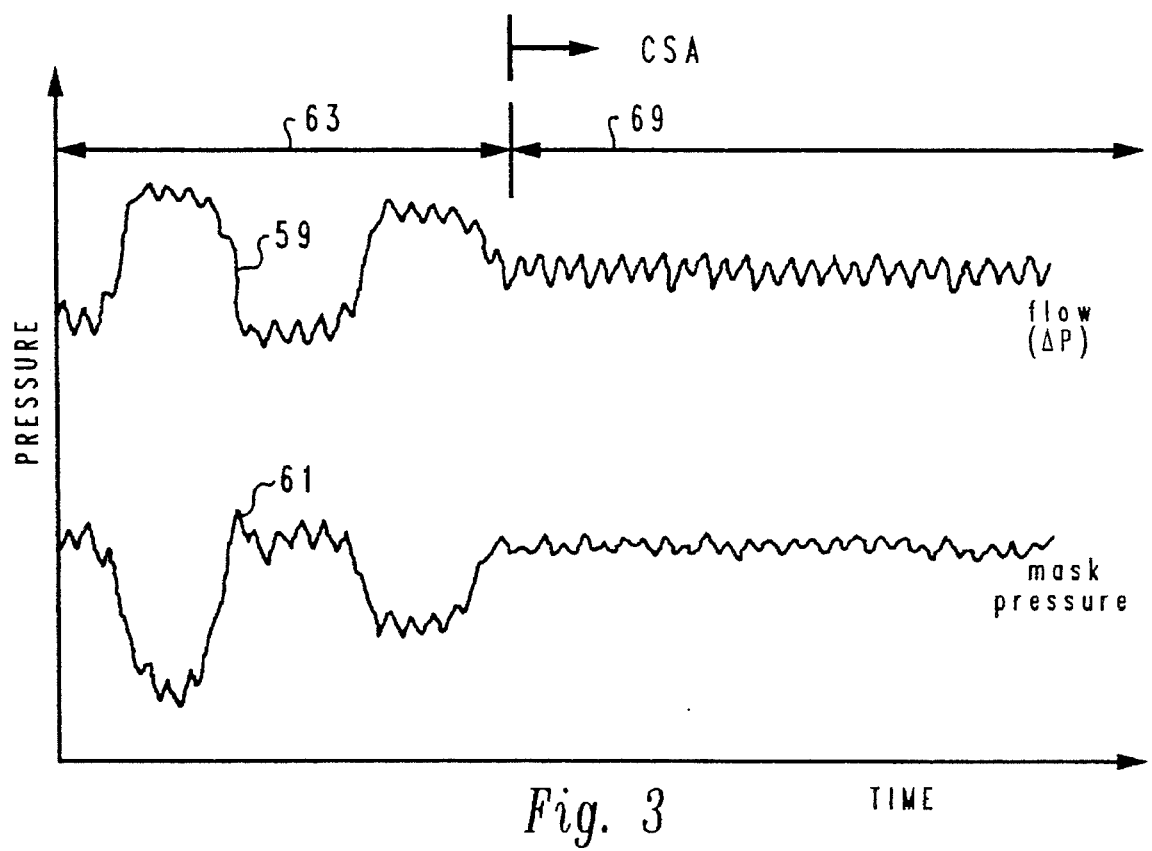
FIG. 3 is a pair of graphs, one illustrating the difference in pressure that exists between the mask and the compressor output and the other illustrating the mask pressure during an occurrence of central sleep apnea.

In FIG. 3, numeral 69 indicates an occurrence of CSA. In CSA, the brain has signaled the body to stop breathing. Because the upper airway is open, the lungs function as a reservoir. Consequently, the pressure difference measurement of the 5 hertz modulation during CSA is larger than that observed during OSA. Conversely, the mask pressure measurement of the 5 hertz modulation during CSA is less than that observed during OSA.

Delta P curve 59 has a normal breathing section 63 just as in FIG. 2. However, section 69 indicates that breathing has stopped. The delta P curve 59 becomes almost constant. This indicates that there is no dynamic pressure changing due to a person's breathing, and thus the difference between the pressure sensing tubes 46 and 47 will be almost constant, except for the pressure variations due to 5 Hz modulation.

If that condition occurs, there will be essentially no cycles above a noise threshold level to compute areas upon and compare to the average area of the past 50 breath cycles. The microprocessor 57 in this instance will initiate a delay, preferably ten seconds. If at the end of the delay breathing has not resumed, the microprocessor 57 increases pressure in attempt to alleviate the condition in the same manner as described previously. Also, the microprocessor 57 will attempt to determine whether the condition of lack of breathing is due to central sleep apnea (CSA) or obstructive sleep apnea (OSA). In obstructive apnea, breathing passageways are blocked. In central apnea, the brain has ceased signaling the body to breathe. In the case of central apnea, the passageways are still open.

The curves shown in FIGS. 2 and 3, illustrate the difference in both the patient mask pressure and the delta P pressure signals for OSA and CSA. Specifically, the 5 Hz modulation frequency present in the mask pressure is accentuated and delta P diminished when OSA occurs. This is due to the fact that during OSA the airway is obstructed reducing the overall airway volume and increasing its resistance. Conversely, during CSA changes in delta P and mask pressure due to the 5 Hz modulation pressure resemble normal breathing. Detection of CSA is accomplished by noting that flow through hose 41 has stopped.

Figure 4:
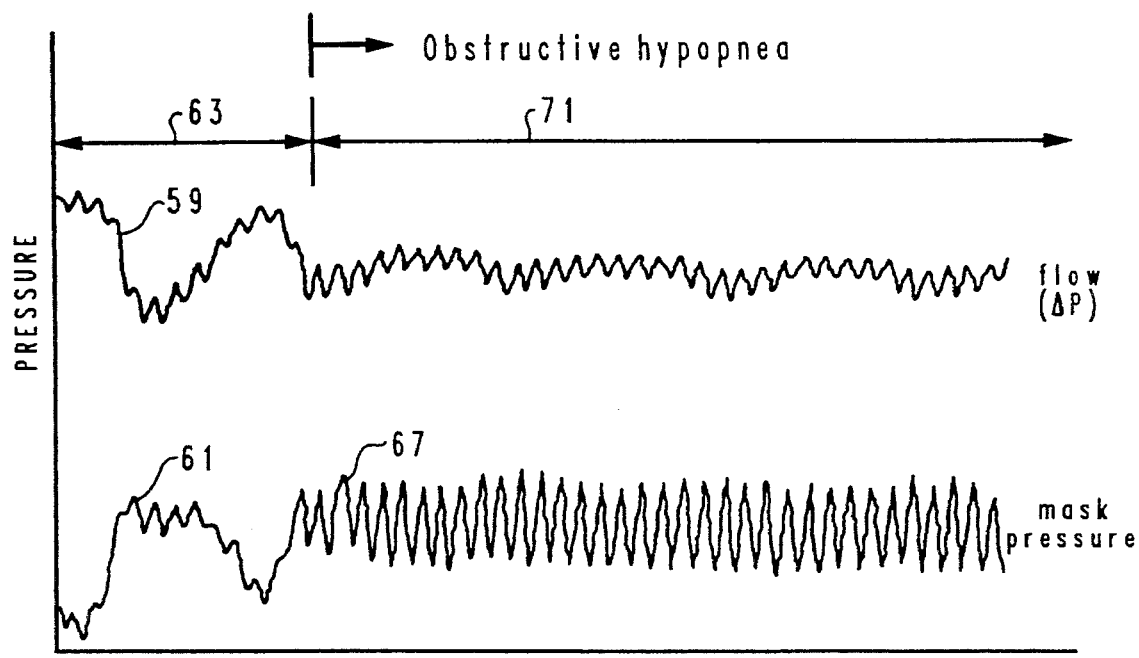
FIG. 4 is a pair of graphs, one illustrating the difference in pressure that exists between the mask and the compressor output and the other illustrating the mask pressure during an occurrence of obstructive sleep hypopnea.

Referring to FIG. 4, a milder form of OSA called obstructive sleep hypopnea, or OSH, is illustrated. OSH is a partial obstruction of the upper airway, which allows some air to pass. In the episode 71 of OSH, there is some pressure difference in hose 41 varying at a low frequency due to breathing. However, the amplitude of the pressure difference 59 is much less in OSH 71 than in normal breathing 63. Mask pressure 67 reflects the 5 hertz modulation.

In FIG. 4, section 63 represents normal breathing, while section 71 represents partially obstructed breathing or obstructive hypopnea. The amplitude of delta P curve 59 in region 71 is much less than before. The reason is that due to the partial obstruction, there will be less flow of air into and out of the person. The difference in pressure between sensing tubes 46, 47 is considerably less in section 71 than in section 63.

When hypopnea is detected Microprocessor 57 will ordinarily signal compressor 43 to increase the output upper pressure first in an attempt to alleviate that condition. If the hypopnea is not eliminated then the upper pressure will be increased further until the maximum allowed pressure is reached. Furthermore, the output pressure will be reduced if the condition ceases to exist after a selected time period. Hypopnea can occur and be detected with the delta P measurements even though no other sleep disorder breathing signals are occurring.

Figure 5:
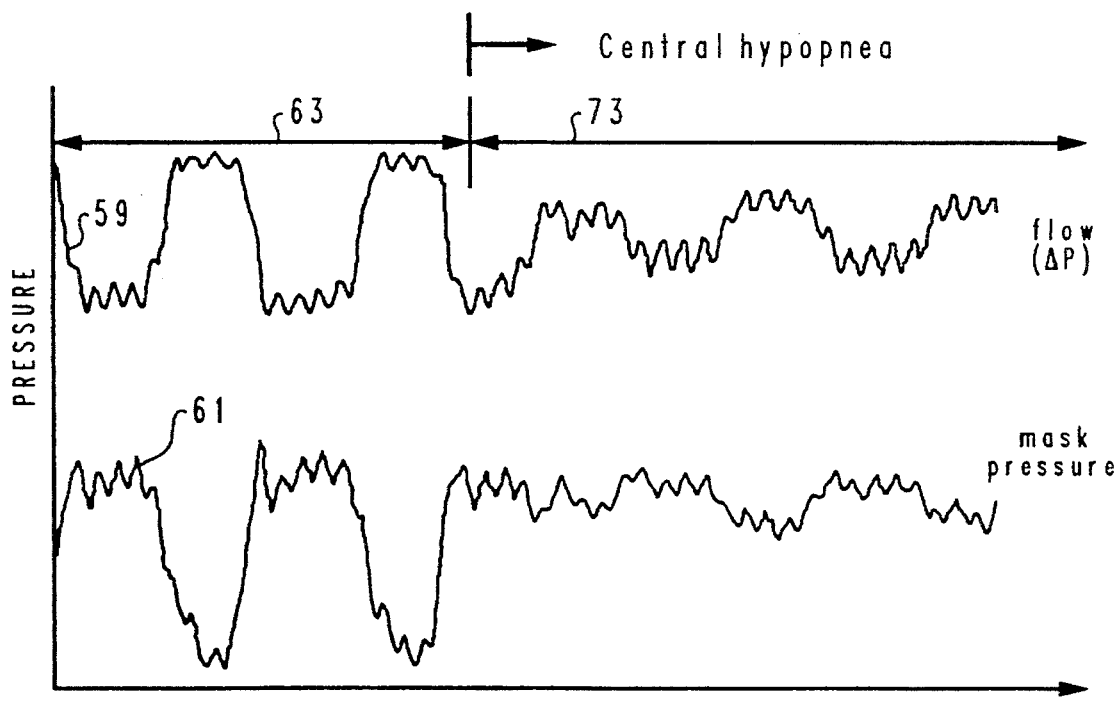
FIG. 5 is a pair of graphs, one illustrating the difference in pressure that exists between the mask and the compressor output and the other illustrating the mask pressure during an occurrence of central sleep hypopnea.

FIG. 5 depicts Central Sleep Hypopnea (CSH), which is a milder form of CSA. CSH is characterized by shallow breathing, although there is no blockage of the upper airway. Pressure differences occurring in hose 41 are reduced substantially relative to those occurring during normal breathing in 63. Mask pressure fluctuates, but because the upper airway is open, the 5 hertz modulation of pressure will be the same as the case of breathing with no obstruction 63.

Tables 1–2 provides command pressure components and indicates the combinations of events indicating a condition to be treated.

The processes described with reference to the flow charts of FIG. 9–29 include various diagnostic determinations. The basic determinations are set out in Table 1. The letters relate into graphic depictions of the conditions shown in FIGS. 6–8.

TABLE 1

A - No pharyngeal wall vibration and power on
B - Pharyngeal wall vibration occurring
C - Central or obstructed sleep hypopnea
D - Central or obstructed sleep apnea
E - Normal breath volume
F - Complete pharyngeal closure
G - Partial pharyngeal closure
H - Upper airway open
I - Mask off
J - Mask leak TABLE 1-continued O - Power on
P - Power off Complete diagnosis for purposes of treatment or response requires combining of several basic indications as set out in Table 2.

TABLE 2

| CONDITIONS | DIAGNOSIS |
| --- | --- |
| A + E + H | Normal breathing |
| B + E + H | Pharyngeal wall vibration (PV) only |
| A + C + H | Central hypopnea |
| A + C + G | Obstructive hypopnea |
| A + D + H | Central apnea |
| A + D + F | Obstructive apnea |

FIG. 6 illustrates various abnormal breathing conditions and the modification of command pressure to treat the conditions as they occur. The upper curve 601 is a pressure difference measurement showing breathing over a period of time including sessions of normal breathing, indicated by conclusions A, E and H, pharyngeal wall vibration (B+E+H) and obstructive hypopnea (A+C+G). During the first period of normal breathing, the command pressure to the compressor 43 (FIG. 1) is at a minimum level indicated by curve 603 and is not varied with inspiration and expiration cycles. Pharyngeal wall vibration, indicated by "PV", is shown occurring during the inspiration and expiration cycles of breathing. This higher frequency wave form is detected through standard deviation calculations. After detection of pharyngeal wall vibration, command pressure 603 begins to follow inspiration and expiration cycles of the patient, with inspiration command pressure being substantially boosted over expiration command pressure. The command pressure 603 is raised after detection pharyngeal wall vibration signals 93, where the time between pharyngeal wall vibration signals does not exceed 20 seconds. The command pressure includes an inspiration level, set at a first increment of pressure component level P3 (Press 3), and an expiration level which here returns to base pressure. Expiration command pressure can be boosted over minimum levels under certain circumstances, however. After normal breathing returns or is restored, overall command pressure 603 is reduced, first by cutting inspiration cycle pressure, followed by elimination of the inspiration cycle boost and concluded with gradual reduction in base pressure to minimum levels.

Referring to FIG. 7, occurrences of OSH and OSA are illustrated. After the onset of OSH, command pressure 703 is increased for inspiration levels by adjustment of a pressure component level P2 (or Press 2). However, the difference between the inspiration level and base pressure is not allowed to exceed a maximum differential.

During OSA, the base level of command pressure 703 is ramped up in steps as long as it does not exceed a maximum permitted base pressure level. Obviously, inspiration is not occurring during apnea, so no variation in command pressure due to inspiration and expiration occur. FIG. 7 also shows episodes of normal breathing, and pharyngeal wall vibration and obstructive hypopnea.

FIG. 8 shows episodes of central hypopnea and apnea in pressure waveform 801. In the case of central hypopnea, the base pressure level of command pressure 803 remains constant. If breathing remains shallow for ten seconds, an inspiration cycle appears and its level gradually increases until normal breathing reappears. During the occurrence of central apnea, the command pressure 803 remains constant.

Figure 9:
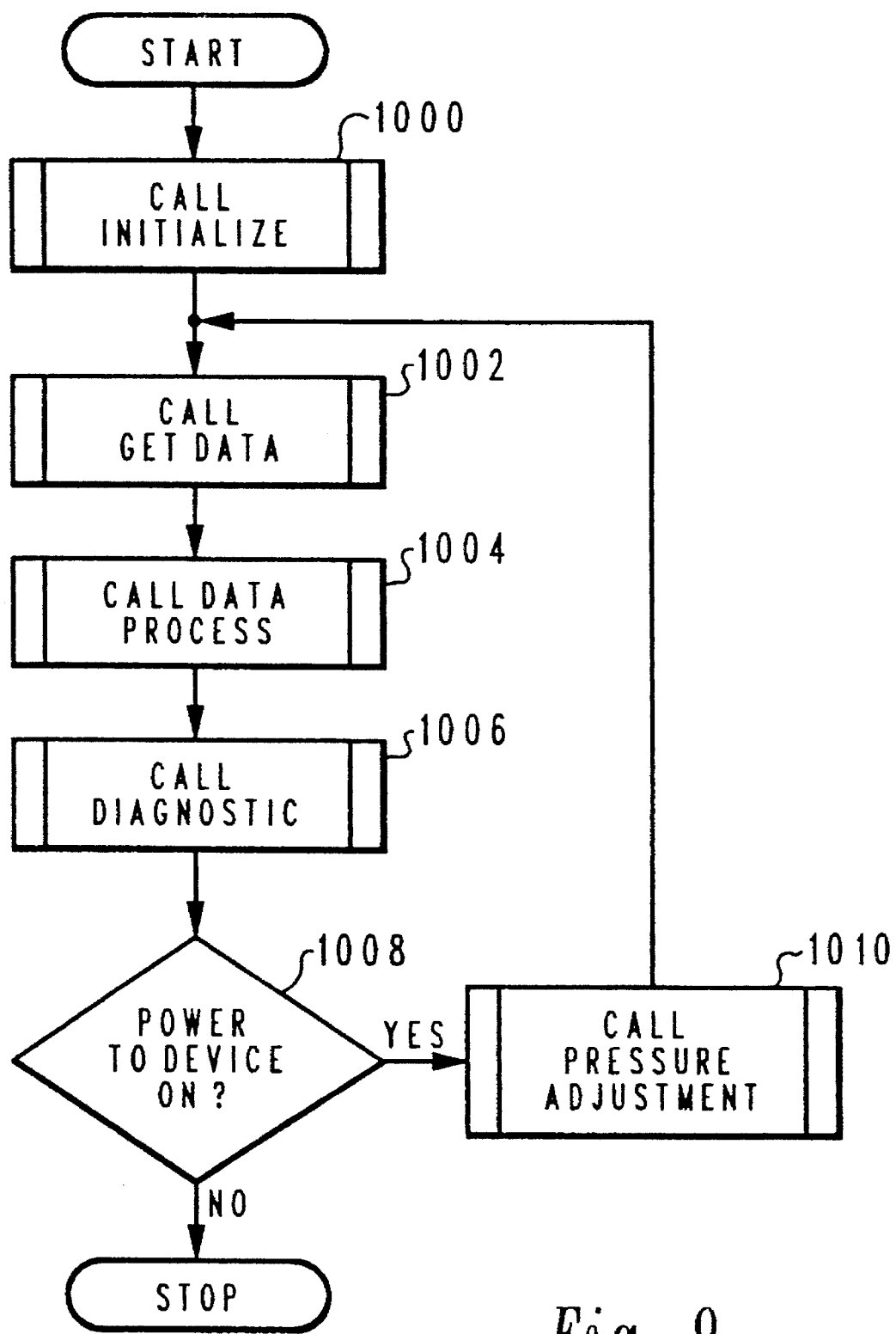

FIG. 9 is a logical flow chart illustrating a main program for microprocessor 57. The main program is used to control flow of the process among a plurality of subroutines relating to the acquisition of data from mask 39 and hose 41, the processing of that data, the use of the processed data for diagnostic purposes and the control of air pressure applied to the mask. The main program is entered at step 1000 with a call to initialize various variables, arrays and flags used by the subsequent data acquisition, data processing, diagnostic and pressure adjustment subroutines. Then step 1002 is executed to call a Getdata subroutine in which data is retrieved from an analog to digital converter 55 and organized for use by the data processing and diagnostic subroutines. Step 1004 is a call to the data processing subroutine. Step 1006 is then executed to call the diagnostic subroutine. Finally a test is done to determine if power to the compressor for the mask is still on at step 1008. If power is on, step 1010 is executed to call a pressure adjustment subroutine. Processing is then returned to step 1002. If compressor power was off at step 1008, the NO branch is followed to discontinue execution of the program.

Figure 10:
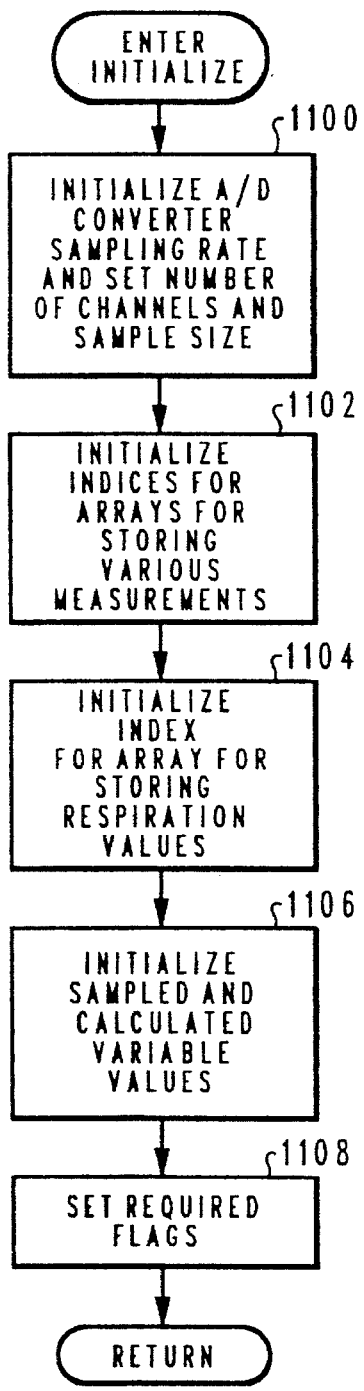

FIG. 10 is a logical flow chart illustrating a subroutine for initialization of assorted variables and flags used by subsequent subroutines described herein. The subroutine is entered at step 1100 with initialization of an analog to digital converter sampling rate and the setting of the number of channels and sample size used. In the preferred embodiment, analog to digital converter 55 samples the pressure difference along hose 39 and the mask pressure 4000 times a second. There are two channels, corresponding to the pressure difference and mask pressure signals respectively. The data is stored to two arrays each sized for 400 such sample points corresponding to a sampling interval. Step 1102 is executed to initialize indices for a pressure difference array and mask pressure array to which the values from the channel arrays will be transferred. In step 1104 an index is initialized to an array used for storing measurements of the area between the delta P curve and the base line. The size of this array is 50. In step 1106 a number of sample and calculated variable values are initialized. The specific variables used will be introduced in the discussion of the appropriate subroutines. Similarly at step 1108 initial values for a number of flags are set. Again specific flags will be described at the time of the discussion of the appropriate subroutine. After step 1108 processing is returned to the main program.

Figure 11:
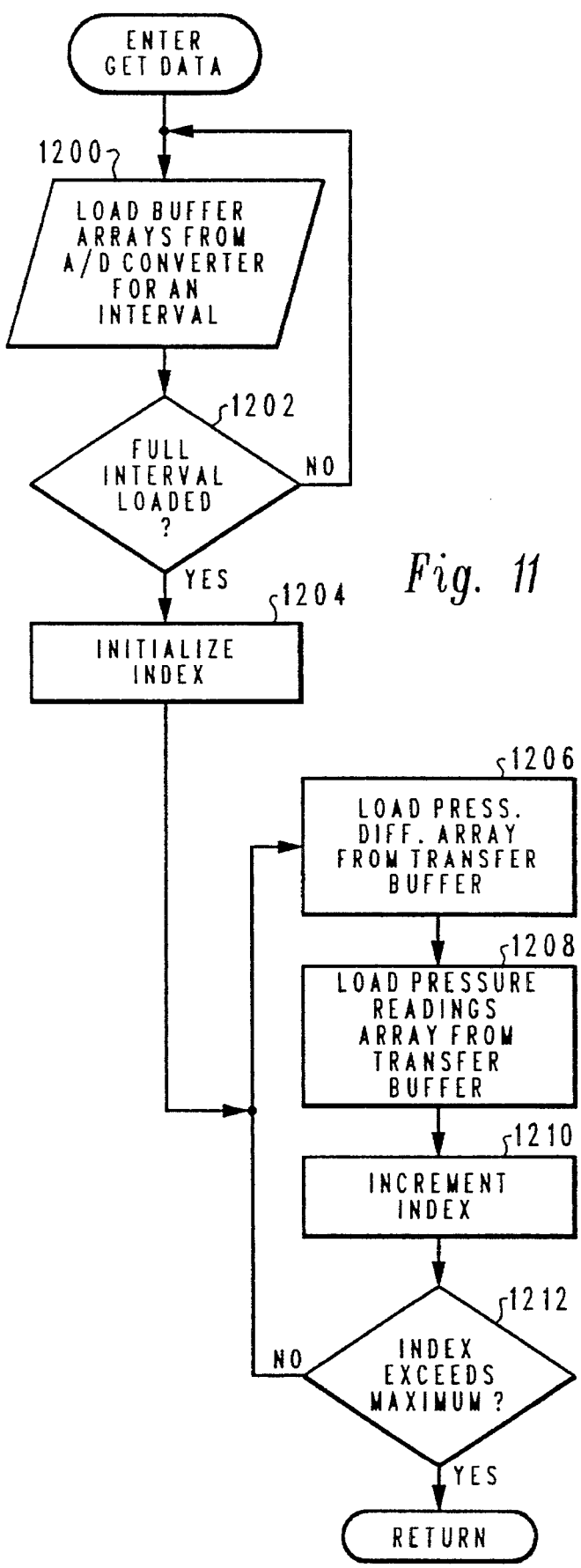

FIG. 11 is a logical flow chart illustrating acquisition of data by microprocessor 57 from A/D converter 55. Step 1200 is an input/output step corresponding to the transfer of data to buffer arrays from the analog to digital converter for an interval of 400 samples. Step 1202 controls looping through step 1200 until a full interval has been loaded into the buffer arrays. Once a full interval of samples has been transferred to a buffer array, step 1204 is executed to initialize an index. Until a full interval of samples has been accumulated the process loops from step 1202 back to step 1200. Next, step 1206 is executed to transfer data from one buffer array into a pressure difference array. This array is sometimes also referred to as a delta P array. In step 1208 mask pressure readings are loaded into a pressure reading array from the transfer buffers. Step 1210 provides for incrementation of the index in use. Step 1212 controls looping of the transfer process back through step 1206. Once the index exceeds in size a buffer array the YES branch is followed to the return the processing to the main program of FIG. 9.

Figures 12, 13:
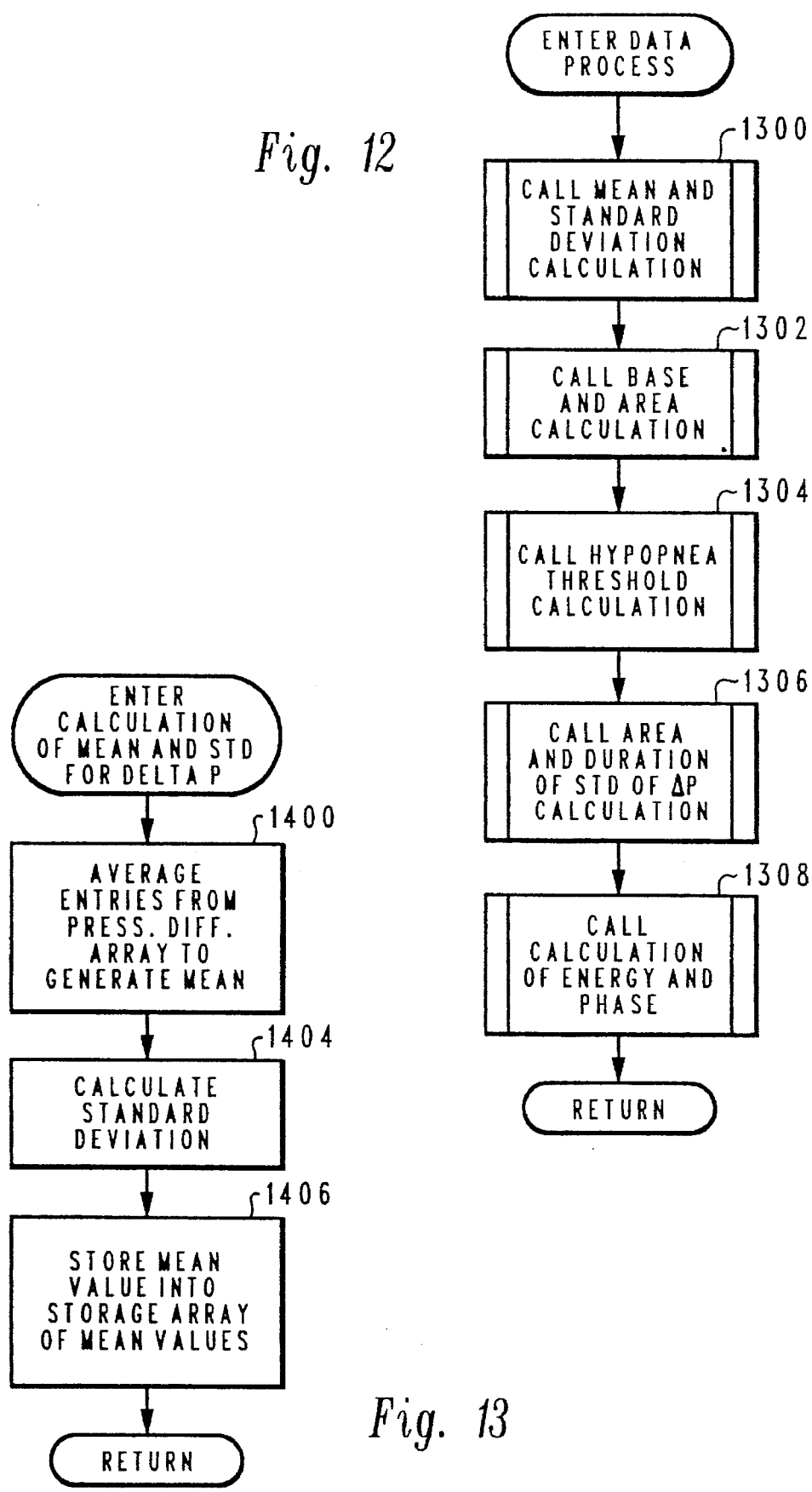

FIG. 12 is a logical flow chart illustrating a data processing subroutine. The data process subroutine consists essentially of a series of calls to five calculation functions. These functions include a subroutine for calculation of a mean value and a standard deviation value for the samples in the pressure difference array (step 1300). Step 1302 is a call to a function for the calculation of a baseline and the area of the mean value of the pressure difference array. Step 1304 is a call to a subroutine for calculation of a hypopnea threshold using the previously calculated mean. Step 1306 is a call to a calculation of the area and duration of the standard deviation of the delta P signal. Step 1308 is a call to a subroutine for calculation of the energy and phase of the pressure difference and mask pressure at a frequency of 5 hertz. The subroutine is then exited back to the main program.

FIG. 13 is a logical flow chart illustrating the subroutine used for the calculation of the mean and standard deviation of a set of samples from a pressure difference array. The process is entered with step 1400 with determination of the average value of the entries in the pressure difference array. In step 1404, the standard deviation is calculated using the mean and mean square values previously determined. Next, step 1406 is executed to store the mean value into a storage array of pressure difference mean values having a size of 400. This group of values is used for calculating an initial baseline. Incrementation of an appropriate index for this array is also done at this time. The subroutine is then exited back to the parent subroutine.

Figure 14:
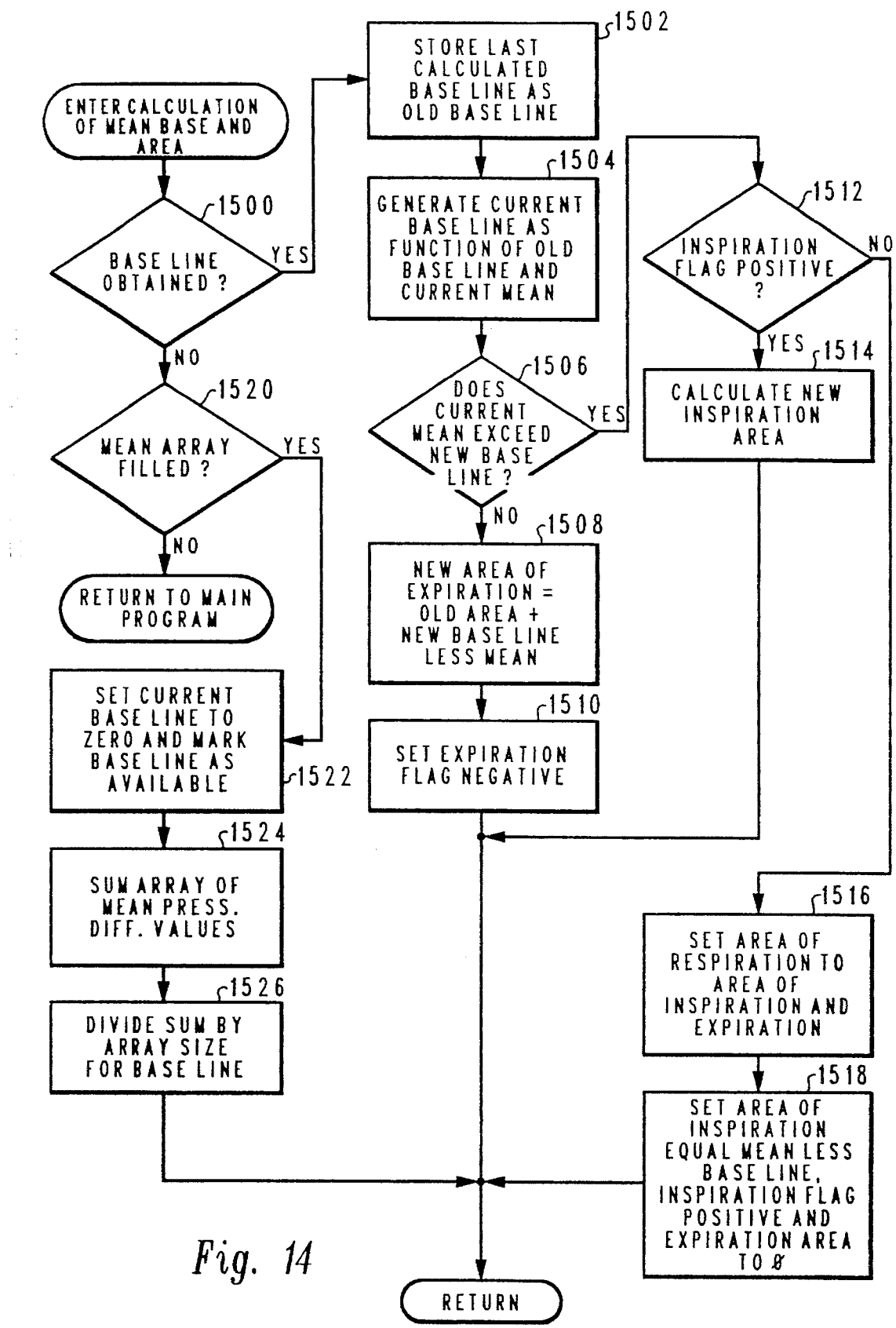

FIG. 14 illustrates a logical flow chart of a subroutine used for calculation of the mean pressure difference baseline and area. Area is a proxy for the energy content of the delta P signal. The process is entered at step 1500 where it is determined if a baseline has already been obtained. If YES, the YES branch is followed to step 1502 where the last calculated baseline is stored as the old baseline. Next, step 1504 is executed to generate a current baseline as a function of the old baseline and the current mean. Next, step 1506 is executed to determine if the current pressure difference mean exceeds the new baseline. If not, a new area of expiration is set equal to the old area plus the new baseline less the current pressure difference mean (step 1508). Next, step 1510 is executed to set the expiration flag to negative and processing is returned to the parent subroutine.

If at step 1506 it is determined that the current pressure difference mean exceeds the new baseline, the YES branch is followed to step 1512 to determine if the inspiration flag is positive. If YES, step 1514 is executed to calculate a new inspiration area equalling the old area plus the mean less the current baseline. Processing is then returned to the parent subroutine. If however the inspiration flag is negative, the NO branch is followed from step 1512 to step 1516. There the area of respiration is set equal to the area of inspiration and expiration. In step 1518 the area of inspiration is reset to equal the pressure difference mean less the baseline. The inspiration flag is set to positive and the expiration area is set to zero. This is done preparatory to the next respiratory cycle.

If at step 1500 it is determined that a current baseline has not yet been obtained, the NO branch is taken to step 1520. At step 1520 it is determined if a completed interval has been acquired. If NO, processing is returned to the main program for acquisition of another interval of sample points. If the array of 100 mean values is completed in step 1520, the YES branch is taken to step 1522 where the current baseline is set to equal zero and an appropriate flag is set to mark a baseline as available. In step 1524 the array of mean values are summed. In step 1526 this sum is divided by the array size to generate a baseline. Processing is then returned to the parent subroutine.

Figure 15:
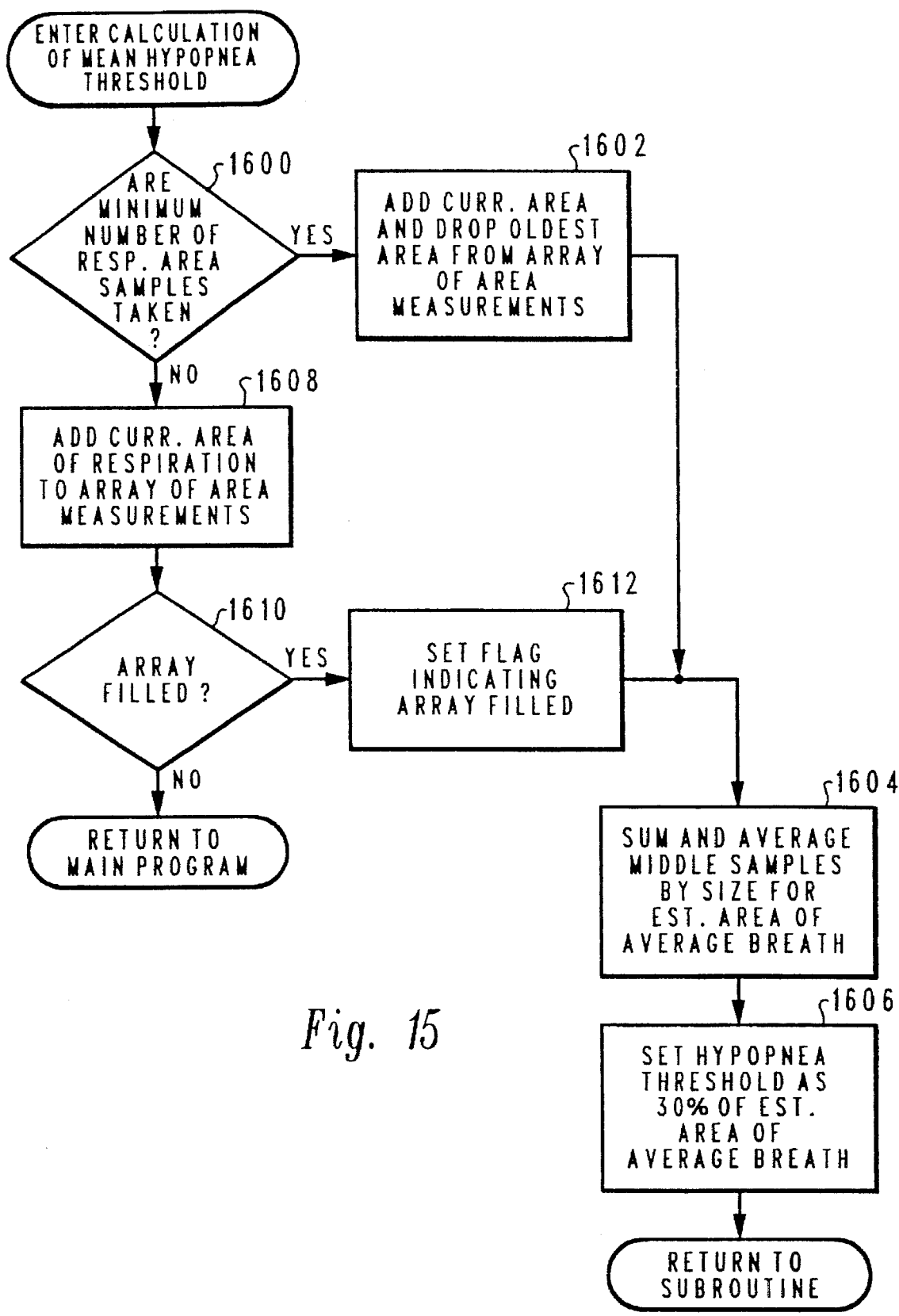

FIG. 15 is a logical flow chart of a subroutine for the calculation of a hypopnea threshold for use in the diagnostic subroutines. The process is entered at step 1600 where it is determined if a minimum required number of measurements for the area between delta P and the base line (referred to as "Area" for brevity) from step 1518 have previously been obtained. If YES, step 1602 is executed to add the latest Area measurement to a First-In, First-Out (FIFO) array of such measurements and to drop the oldest Area measurement from the array. Next, step 1604 is executed to sum and average a set of the measurements. The subset includes the middle 30 by magnitude of the 50 measurements in the FIFO buffer. In step 1606 an hypopnea threshold is established to be equal to 30% of the average of the subset. After step 1606, processing is returned to the parent subroutine. Returning to step 1600, if a minimum number of Area calculations have not been performed, the NO branch is taken to step 1608 where the current measurement is simply added to the array of Area measurements. At step 1610 it is determined if the Area measurement array was filled by the last added entry. Step 1612 is executed to set a flag indicating that the mean pressure difference array is filled. Processing then continues with execution of 1604 as set forth above. Along the NO branch from step 1610 processing is returned to the main program.

Figure 16:
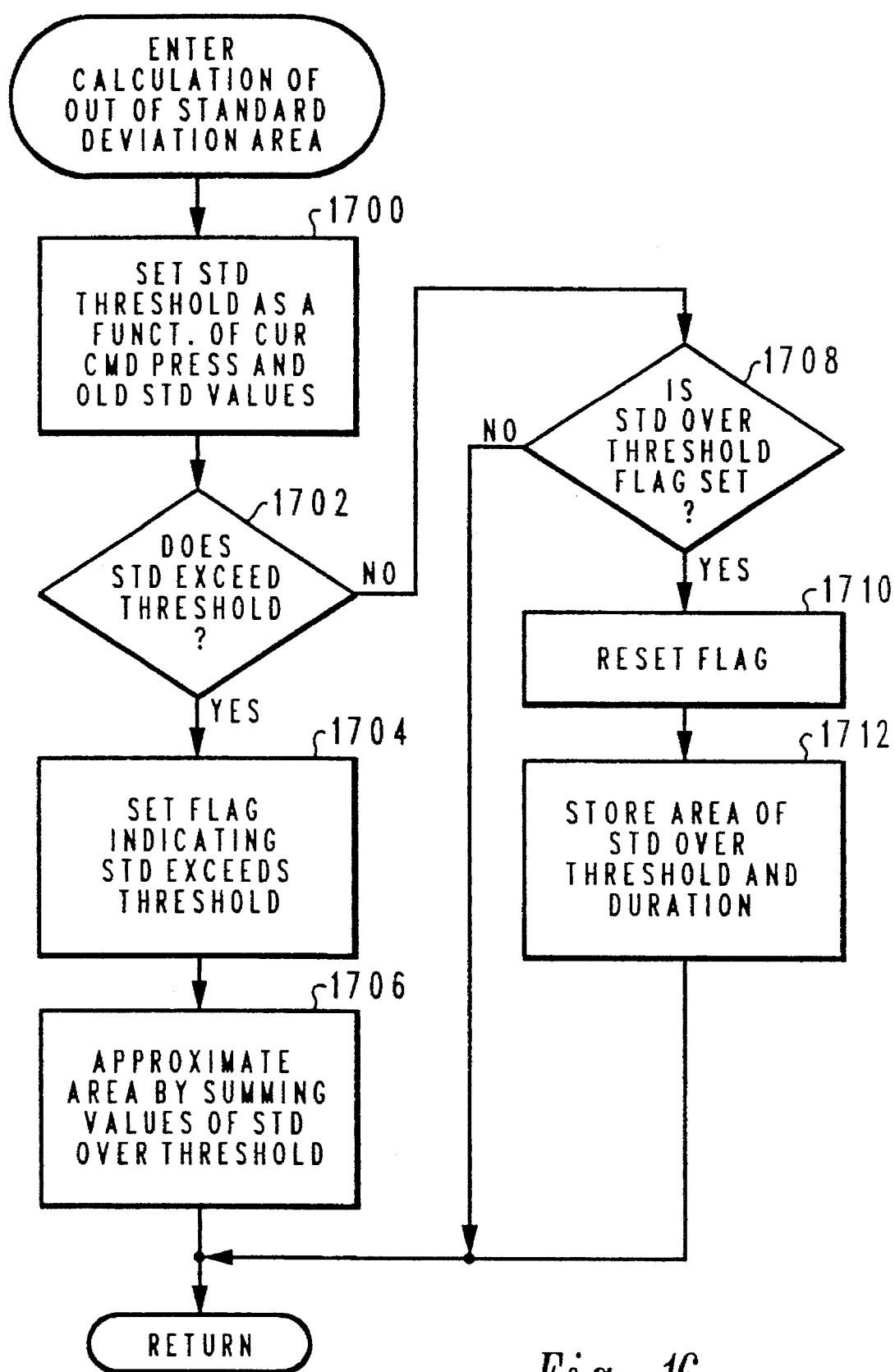

FIG. 16 is a logical flow chart of a subroutine used for the calculation of the area of the standard deviation of delta P which exceeds a threshold. The results are used for detection of pharyngeal wall vibration. The process is entered with execution of step 1700. There a variable called standard deviation threshold is set equal to a function of the current command pressure and old standard deviation values. The calculation of command pressure is described below. Next, in step 1702, it is determined if the current standard deviation exceeds the standard deviation threshold just calculated. If YES, step 1704 is executed to set a flag so indicating and step 1706 is executed to generate a measure of the area of the standard deviation. The measure is equated to an area found by summing the values by which the standard deviations exceed the threshold. If at step 1702 a negative determination has been made, step 1708 is executed to determine if the standard deviation over threshold flag has previously been set. If YES, step 1710 is executed to reset the flag. Step 1712 is then executed to store the area of standard deviation over threshold and duration. If at step 1708 the flag has not been set processing is simply returned to the parent subroutine. After completion of step 1706 or 1712 processing is returned to the parent subroutine.

Figures 17, 18:
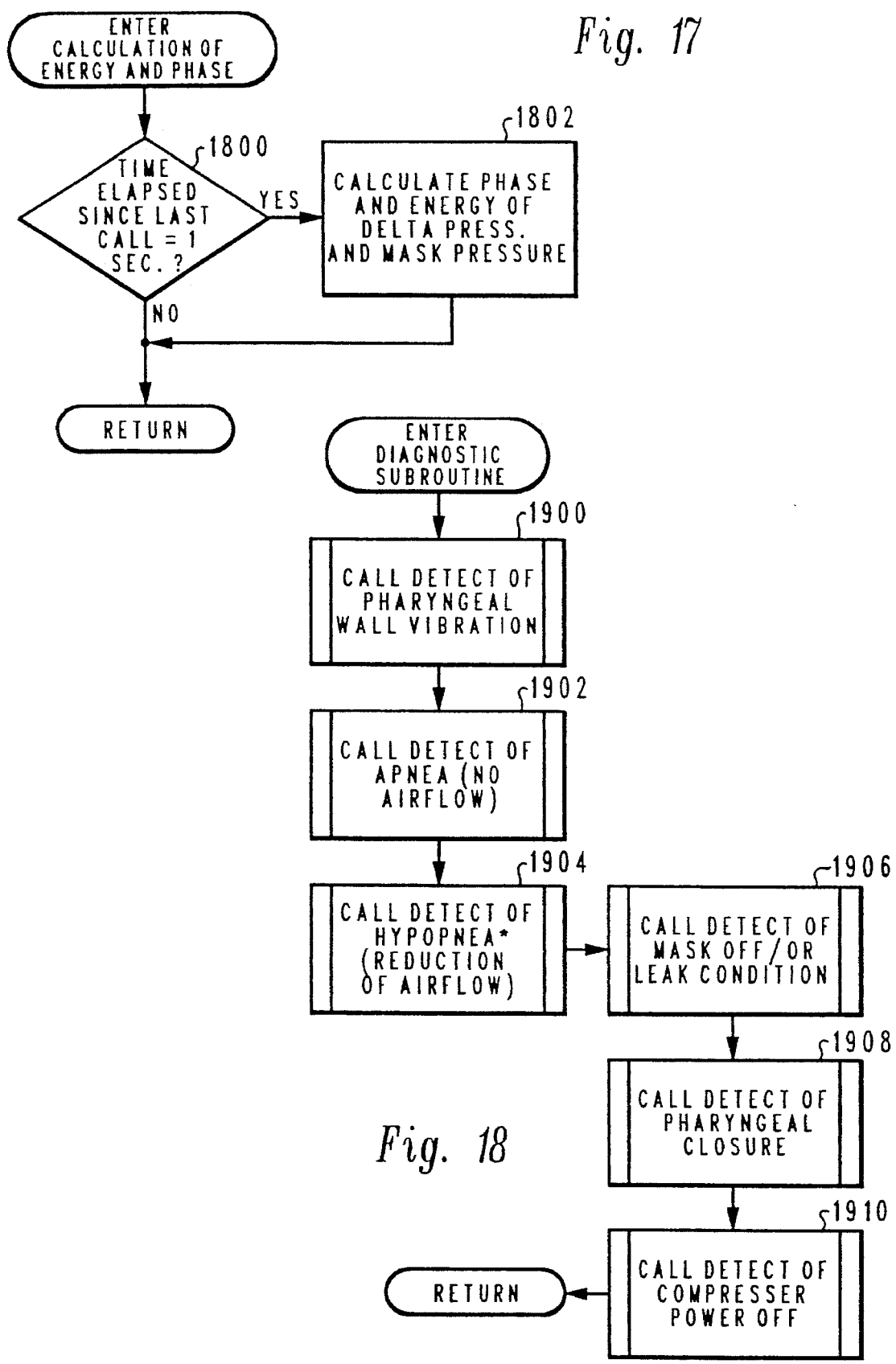

FIG. 17 illustrates a logical flow chart for the subroutine for use in calculation of energy of the 5 Hz signal and phase difference between the pressure and pressure difference signals. The process is entered at step 1800 to determine if one second has elapsed since the last such calculation. If not, the calculation is not done and processing is returned immediately to the parent subroutine. If one second has passed since the last energy and phase measurement, the energy and phase difference calculations are done at step 1802 before return to the parent subroutine.

FIG. 18 is a logical flow chart of a diagnostic subroutine. The diagnostic subroutine includes a plurality of calls used for the detection of various types of obstructed breathing and for detection of leak from or loss of the face mask. Step 1900 reflects a call to a subroutine used for the detection of pharyngeal wall vibration. Step 1902 is a call to a subroutine for the detection of apnea. Step 1904 is a call to a subroutine for the detection of hypopnea. Step 1906 is a call to a subroutine for the detection of a mask off condition or a mask leak condition. Step 1908 is a call to a subroutine for the detection of pharyngeal closure. Step 1910 is a call to a subroutine for the detection of whether compressor power is off.

Figure 19:
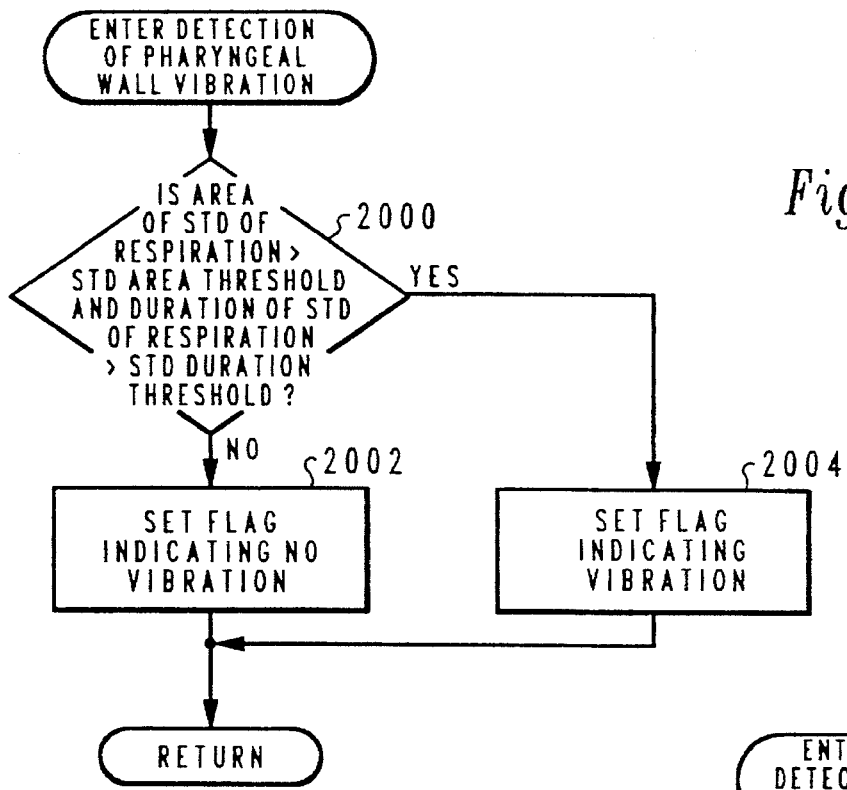

FIG. 19 illustrates a logical flow chart for the subroutine used for detection of pharyngeal wall vibration. Step 2000 is used to determine if the area and duration of the standard deviation of delta P as calculated in step 1700 exceeds a threshold. If not, step 2002 is executed to set a flag indicating no pharyngeal wall vibration is occurring. If YES, a flag is set indicating such vibration at step 2004. After either step 2002 or 2004 processing is returned to the parent subroutine.

Figure 20:
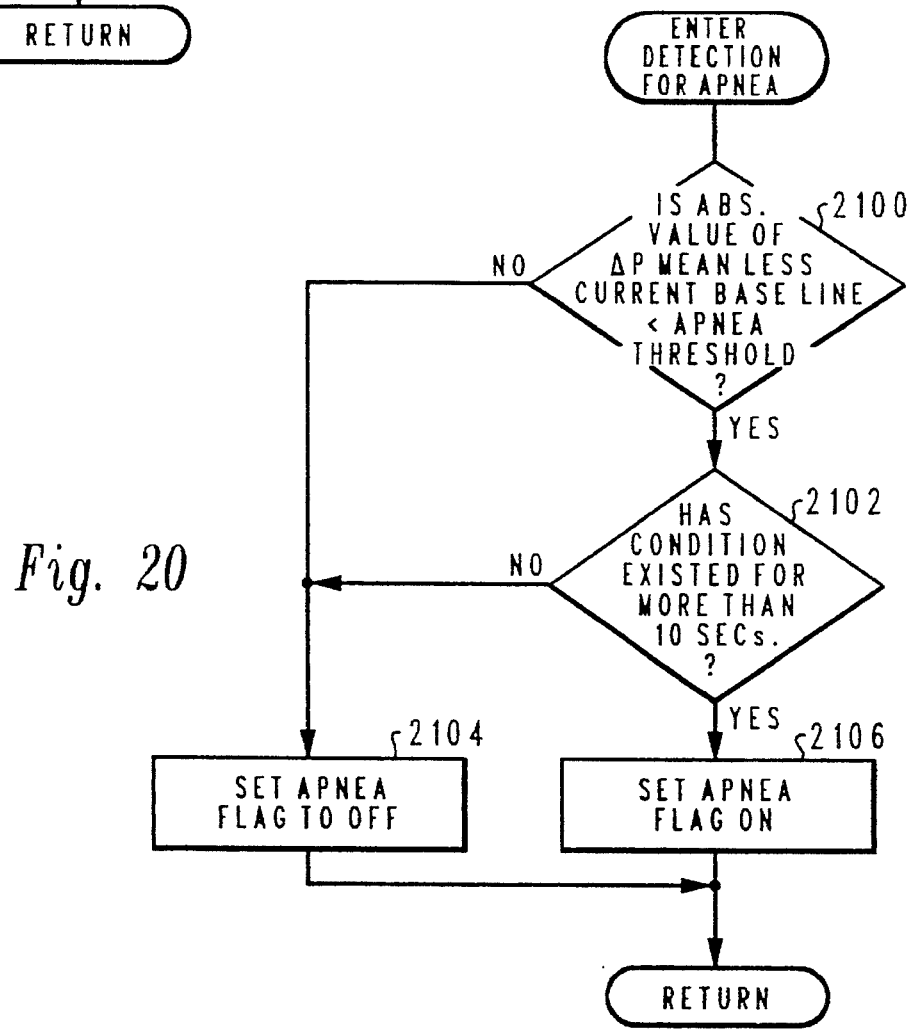

FIG. 20 illustrates a logical flow chart for the subroutine used for detection of apnea. The subroutine is entered at step 2100 with a comparison of the absolute value of the ΔP mean less the current base line with the apnea threshold. If the former is less than the latter, step 2102 is executed to determine if the condition detected at step 2100 has persisted for more than 10 seconds. If the condition has persisted for more than 10 seconds an apnea flag is set to ON at step 2104 and processing is returned to the parent subroutine. If either step 2100 or 2102 is not true, step 2106 is executed to set the apnea flag to OFF and processing is returned to the parent subroutine.

Figure 21:
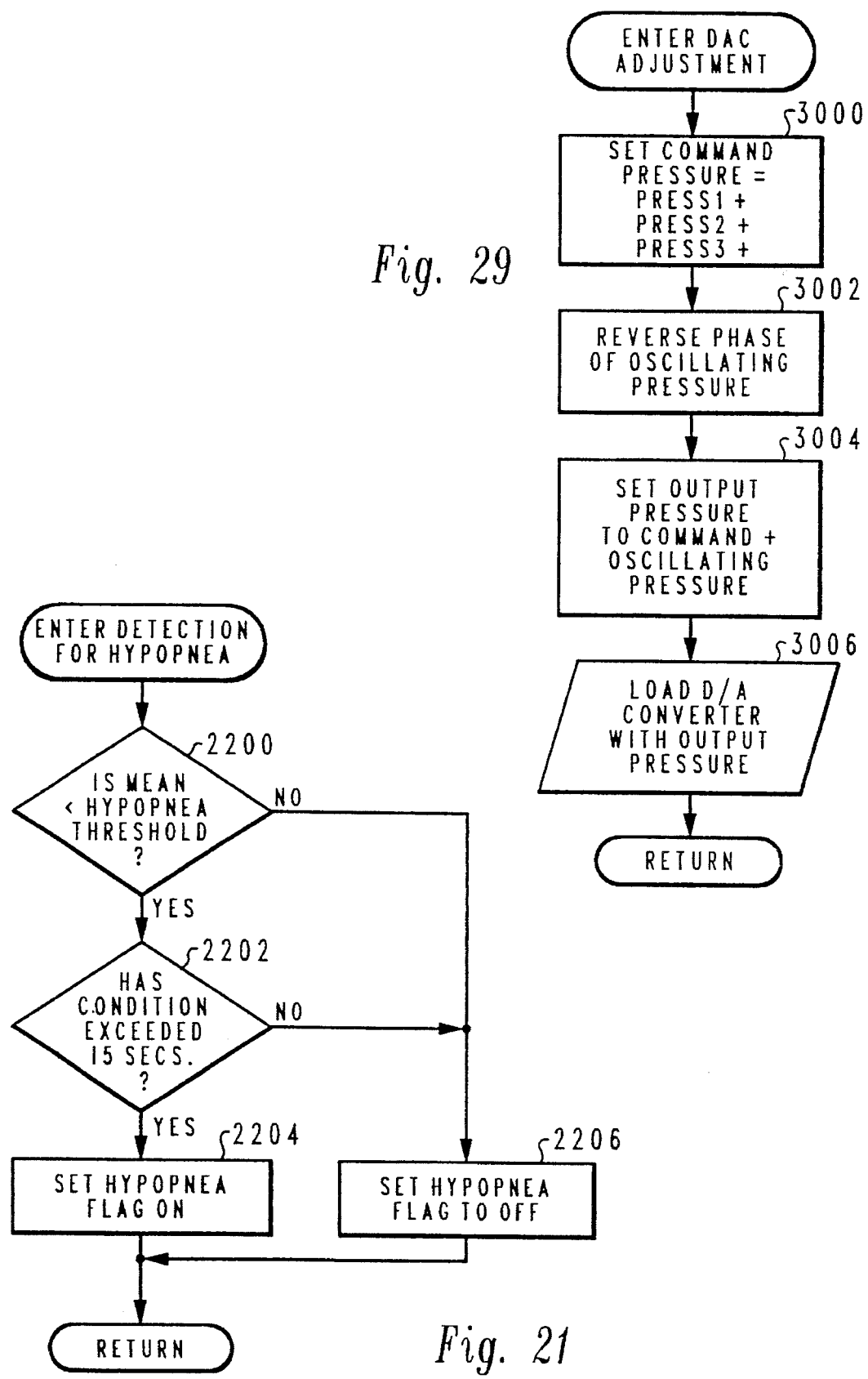

FIG. 21 illustrates a logical flow chart for a subroutine used for the detection of hypopnea. The process is entered at step 2200 where it is determined if the Mean is less than the hypopnea threshold. If YES, step 2202 is executed to determine if the condition has persisted for more than 15 seconds. If the condition has persisted more than 15 seconds, the YES branch is followed to step 2204 to set the hypopnea flag to ON. If either the step 2200 or 2202 conditions are not met, the hypopnea flag is set to OFF by execution of step 2206. After step 2206, the process is returned to the parent subroutine.

Figure 22:
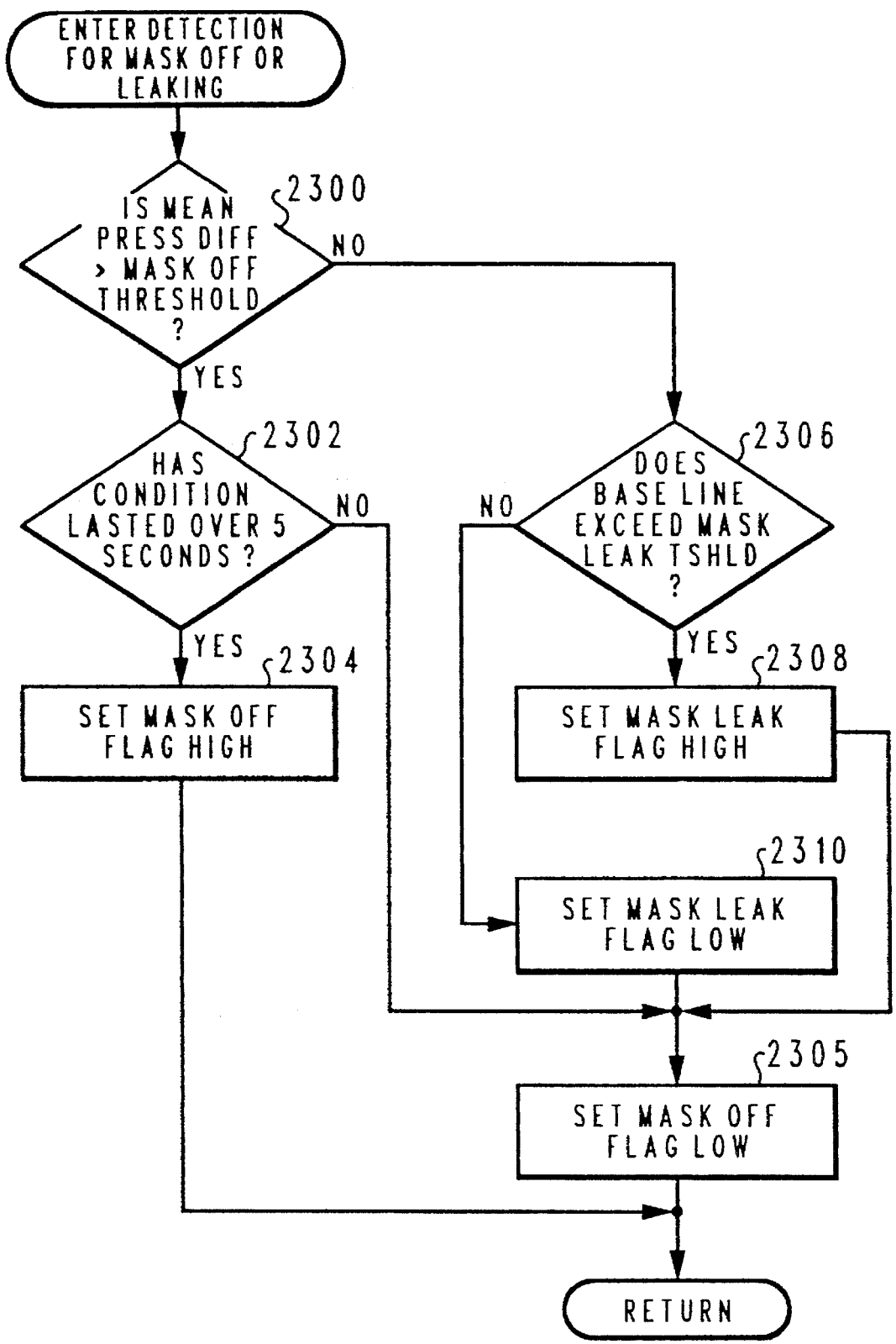

FIG. 22 is a logical flow chart for a subroutine used for detection of a mask off condition or a mask leaking condition. The process is entered with execution of step 2300 where it is determined if the mean pressure difference between sensing tubes 46 and 47 exceeds a mask off threshold. If YES, step 2302 is executed to determine if the condition has lasted more than 5 seconds. If the condition has lasted more than 5 seconds, a mask off flag is set to high at step 2304 and processing is returned to the parent subroutine. If the condition has not lasted over 5 seconds at step 2302, the NO branch is followed to step 2305 where the mask off flag is set to low before returning processing to the parent subroutine. The NO branch from step 2300 directs processing to step 2306 where it is determined if the baseline exceeds the mask leak threshold. If YES, a mask leak flag is set to high at step 2308. If NO a mask leak flag is set low by execution of step 2310. After either step 2308 and 2310, step 2305 is executed.

Figure 23:
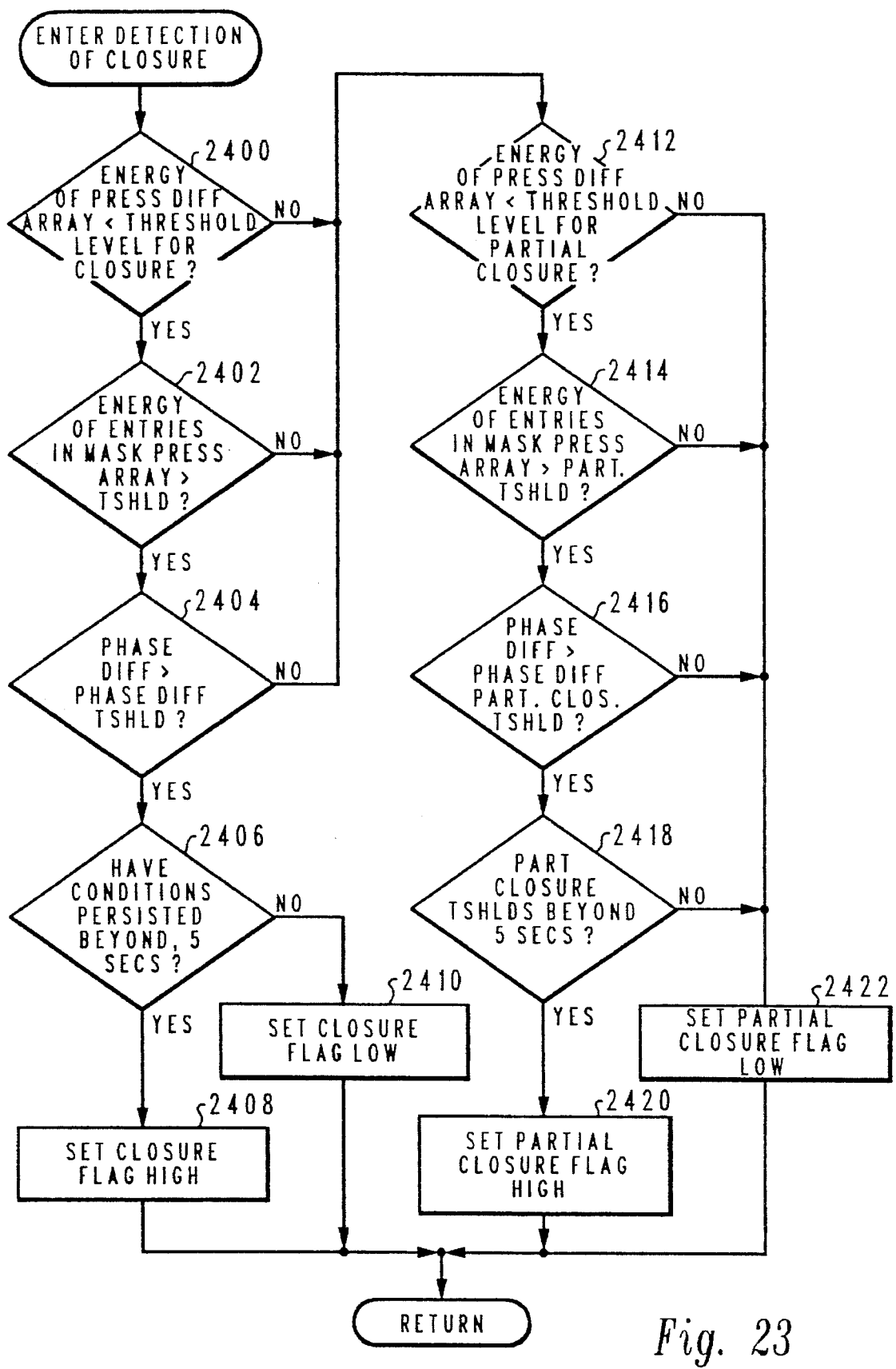

FIG. 23 illustrates the logical flow chart for a process subroutine used for the detection of closure of the breathing path. The process is entered with execution of step 2400 where the energy of the pressure difference array is compared to the threshold level for closure. If the energy of the pressure difference array less than the threshold level, the YES branch is followed to step 2402 where it is determined if the energy of entries in the mask pressure array are greater than a threshold. If YES step 2404 is executed to determine if the phase difference is greater than a phase difference threshold. If YES, step 2406 is executed to determine if the conditions of step 2400, 2402 and 2404 have exceeded 5 seconds. If YES, step 2408 is executed to set the closure flag to high. If the conditions have not yet lasted 5 seconds the NO branch is followed to step 2410 to set the closure flag as low. After completion of step 2408 and 2410 processing is returned to the parent subroutine.

If any of the conditions tested at steps 2400, 2402 or 2404 fail, step 2412 is executed. At step 2412 it is determined if the energy of the pressure difference array is less than the threshold level for partial closure. If it does, step 2414 is executed to determine if the energy of entries in the mask pressure array is greater than a threshold. If YES, step 2416 is executed to determine if the phase difference exceeds a partial closure phase difference threshold. If YES, step 2418 is executed to determine if the conditions of 2412, 2414 and 2416 have persisted beyond 5 seconds. If YES, step 2420 is executed to set a partial closure flag to high. If any of the conditions of 2412 through step 2418 fail, step 2422 is executed to set the partial closure flag low. After either step 2420 or 2422, the processing is returned to the parent subroutine.

Figure 24:
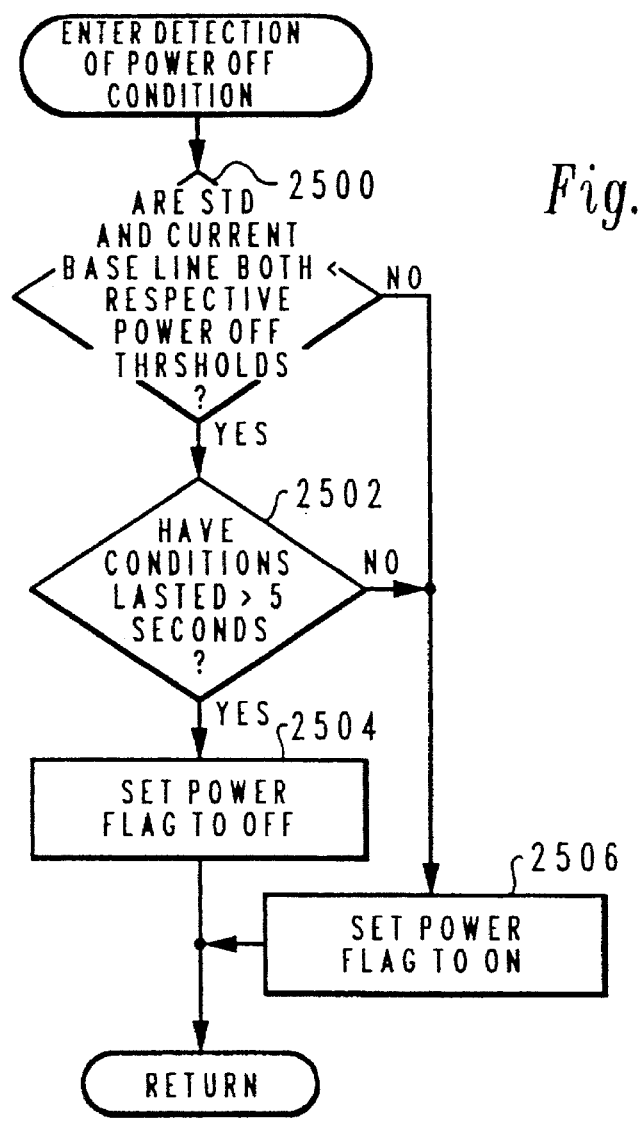

FIG. 24 illustrates a logical flow chart for a subroutine used for the detection of a power off condition of the compressor used to pressurize face mask 39. Entered at step 2500, it is determined if the standard deviation of delta P and the baseline fall below their respective power off threshold levels. If YES, step 2502 is executed to determine if the conditions have lasted more than 5 seconds. If YES, step 2504 is executed to set the power flag to off. Processing is then returned to the parent subroutine. If the result of the tests of step 2500 or 2502 are negative, step 2506 is executed to set the power flag to ON. Processing is then returned to the parent subroutine.

Figure 25:
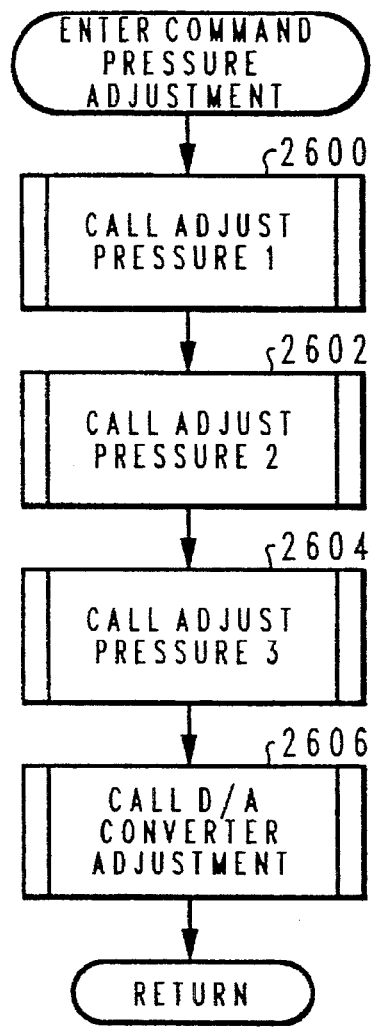

FIG. 25 is a logical flow chart of a subroutine called for adjustment of command pressure. Command pressure is the output requested of compressor 43. The command pressure adjustment subroutine comprises four calls to subroutines. Steps 2600, 2602 and 2604 are calls to subroutines for adjustment of components contributing to the command pressure. Call 2606 provides for combinations of the components to provide command pressure.

Figure 26:
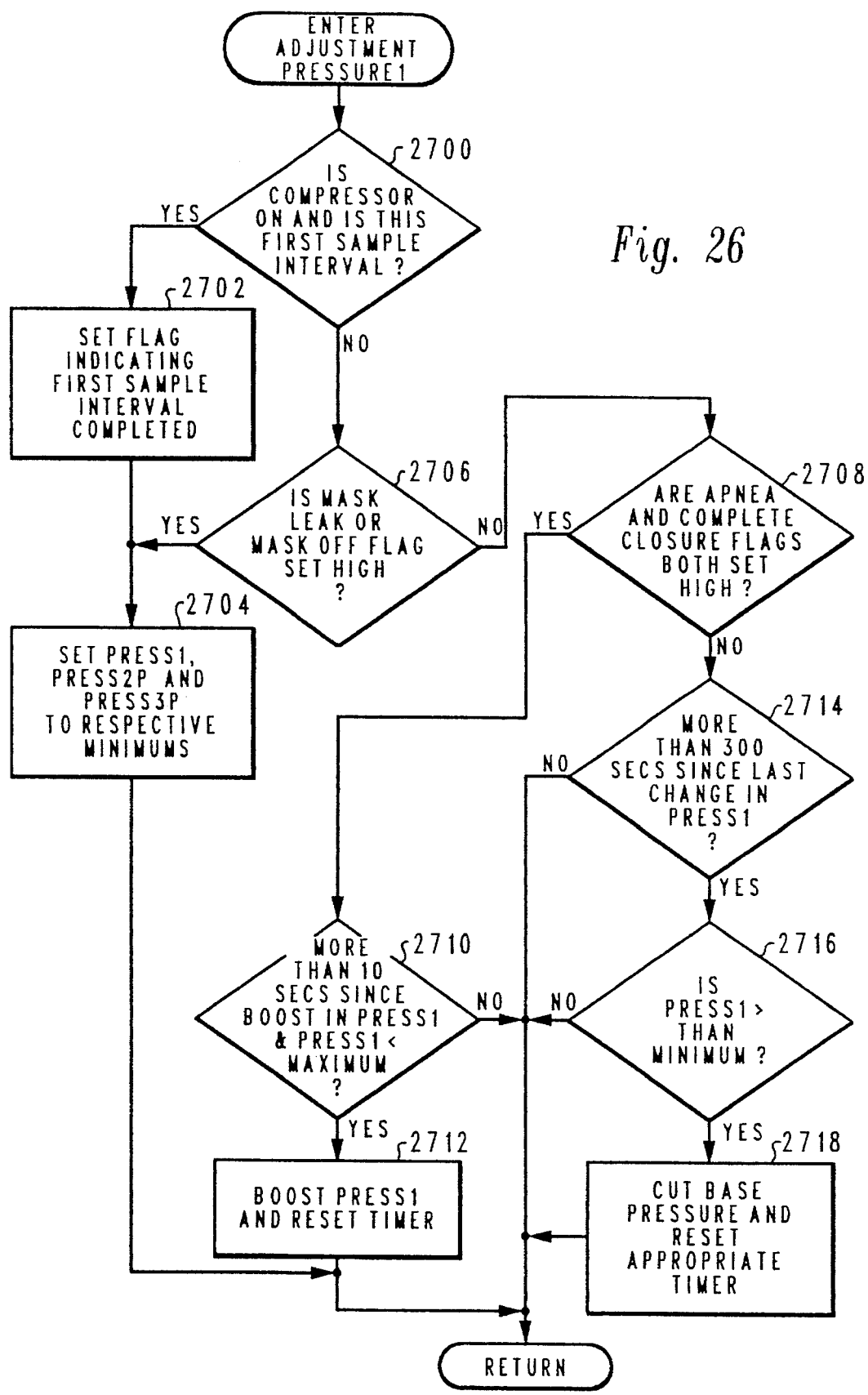

FIG. 26 is a logical flow chart of a process for a subroutine for adjustment of a base pressure level, Press 1. Entered at step 2700 it is determined if the compressor is on and if processing is in the first sample interval. If YES, step 2702 is executed to set a flag indicating the first sample interval is completed. Step 2704 is then executed to set Press 1 and preliminary adjustment components Press 2P and Press 3P to their respective minimum permitted values. Processing is then returned to the parent subroutine. If the result at step 2700 is negative, step 2706 is executed to determine if a mask leak or mask off flag has been set high. If YES, step 2704 is executed as set forth above. If NO, step 2708 is executed to determine if the apnea and complete closure flags are both set high. If YES, step 2710 is executed to determine if more than 10 seconds have passed since the last boost in base pressure and to determine if base pressure is less than the maximum allowed. If both conditions are satisfied, step 2712 is executed to boost base pressure and reset the appropriate timer. Processing is then returned to the parent subroutine. If at step 2710 either condition failed then no further action is taken and processing is returned to the parent subroutine.

If at step 2708 a negative result is obtained, step 2714 is executed to determine if more than 300 seconds have passed since the last change in base pressure. If NO, processing is returned immediately to the parent subroutine. If YES, step 2716 is executed to determine if base pressure is greater than the minimum. If base pressure is equal to minimum, the NO branch is followed to return processing to the parent subroutine. If at step 2716 base pressure exceeded minimum, step 2718 is executed to cut base pressure and to reset the timer used at step 2714. Processing is then returned to the parent subroutine.

Figure 27:
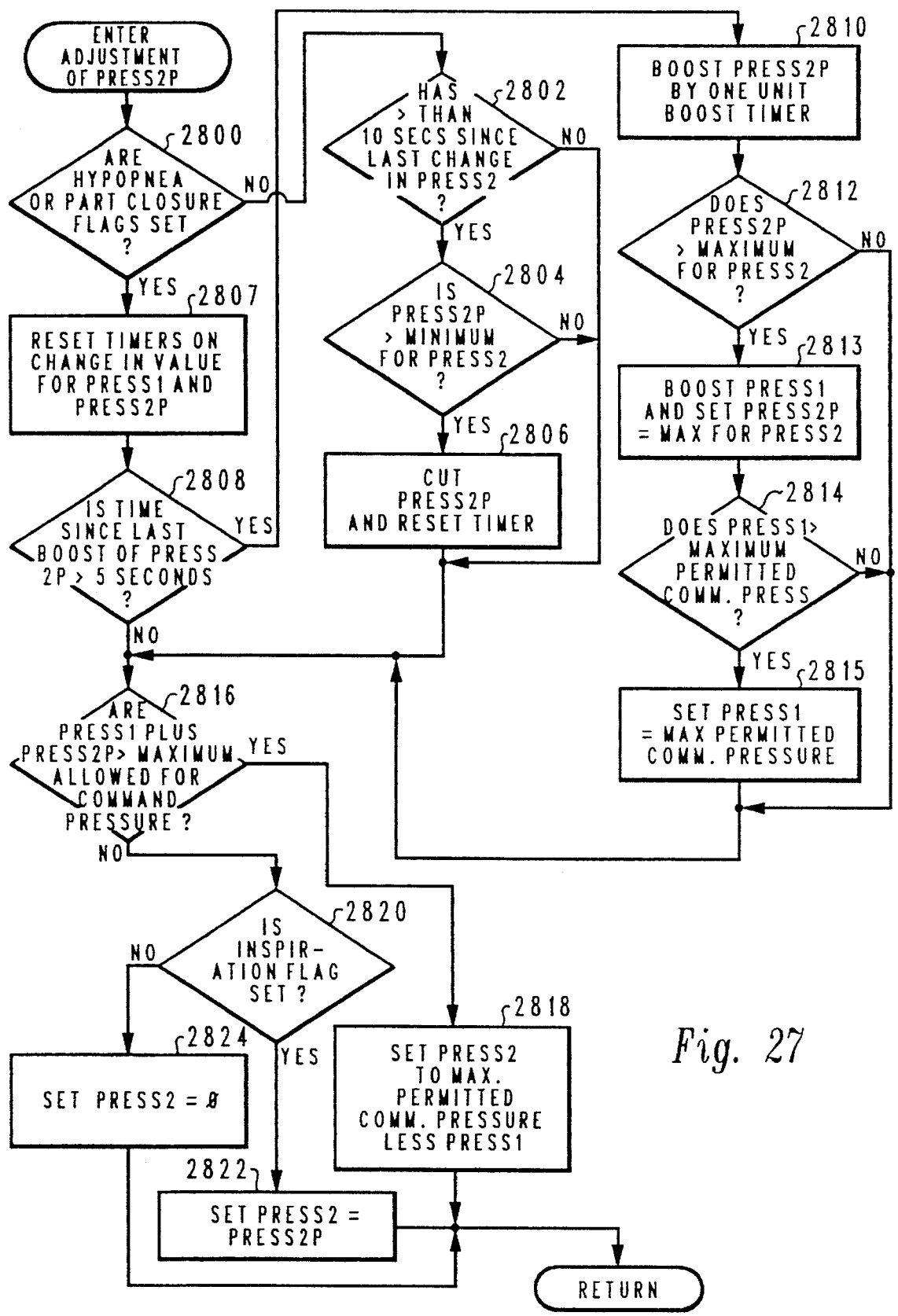

FIG. 27 illustrates a logical flow chart for a subroutine used for the adjustment of preliminary pressure component Press 2P. At step 2800 it is determined if the hypopnea; or partial closure flags are set. If neither flag is set, processing is advanced to step 2802 where it is determined if more than 10 seconds have passed since the last change in Press 2P. If YES step 2804 is executed to determine if Press 2P exceeds its minimum allowed value. If either of the conditions of 2802 or 2804 are not met, processing is immediately advanced to step 2816. Following the YES branch from step 2804, step 2806 is executed to reduce Press 2P and reset of the appropriate timer. Processing then advances to step 2816.

Returning to step 2800 and following the YES branch, step 2807 is executed to reset timers running on Press I and Press 2P. The timers track time elapsed since the last change in value of Press 1 and Press 2P. Step 2808 is then executed to determine if the time elapsed since the last boost of Press 2P exceeds 5 seconds. If YES, step 2810 is executed to boost Press 2P by a unit and the boost timer is reset to zero. Next, step 2812 is executed to determine if Press 2P exceeds its maximum allowed level. If YES, step 2813 is executed to boost base pressure Press I by one unit and to reduce Press 2P to its maximum pertained level. Next, step 2814 is then executed to determine if Press 1 now exceeds maximum permitted command pressure level. If NO, processing advances to step 2816. If YES, step 2815 is executed to reset Press 1 to the maximum permitted value for command pressure. Following the NO branch from step 2812, or after execution of step 2814, the processing is advanced to step 2816. Step 2816 is also executed along the NO branch from step 2808.

At step 2816, the sum of Press 1 and Press 2P are compared to the maximum permitted value for command pressure. Where the sum exceeds the maximum permitted value, the YES branch is taken to step 2818 to set command pressure component Press 2 to the maximum permitted value of command pressure less Press 1. At step 2820, it is determined if the inspiration flag is set. If YES, step 2822 is executed to set Press 2 to Press 2P. If NO, step 2824 is executed to set Press 2 to zero because expiration is occurring. Processing is returned to the appropriate parent subroutine after any of steps 2818, 2822 and 2824.

Figure 28:
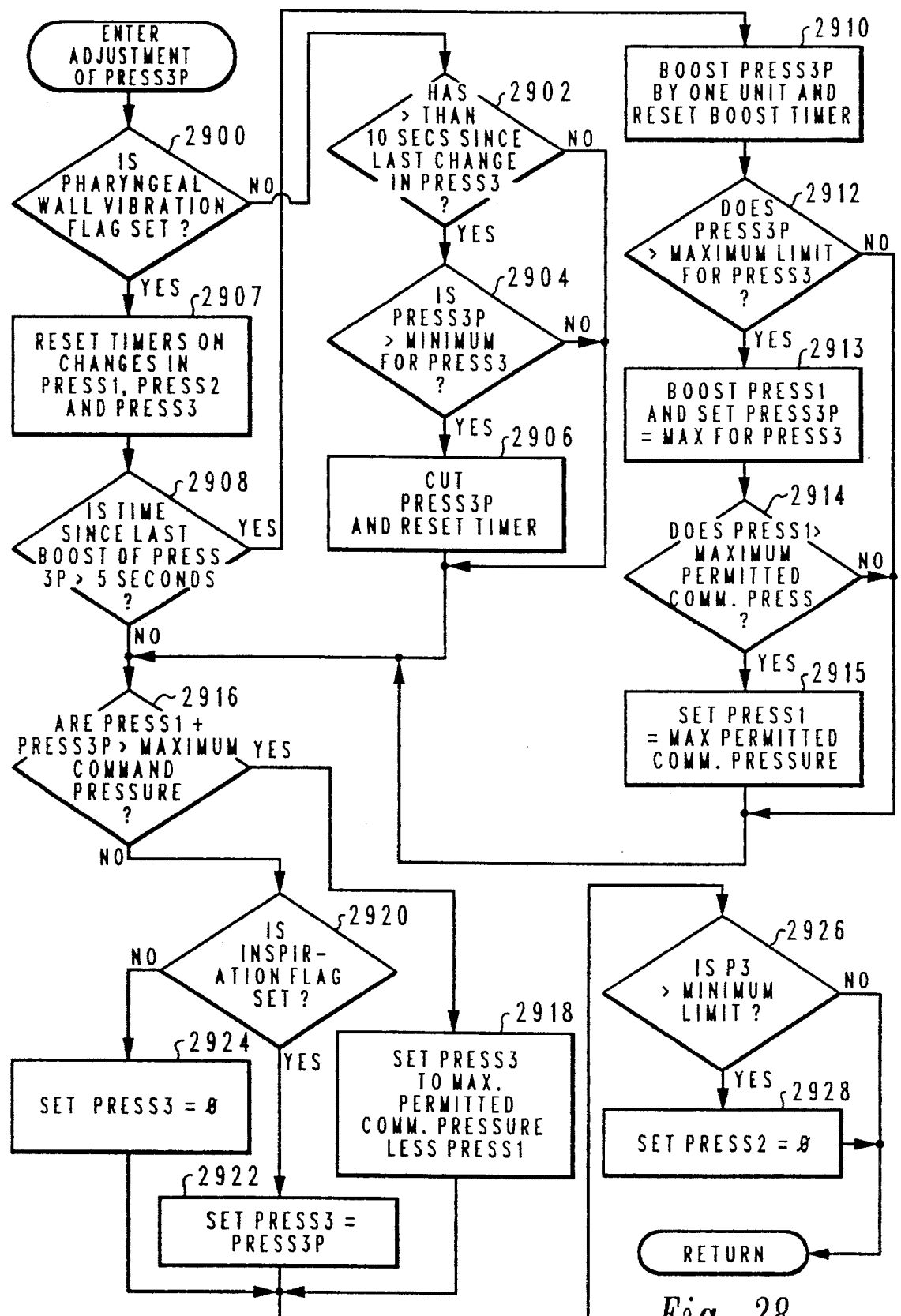

FIG. 28 illustrates a logical flow chart for a subroutine used for the adjustment of preliminary pressure component Press 3P. At step 2900 it is determined if the pharyngeal wall vibration flag is set. If the pharyngeal wall vibration flag is not set, processing is advanced to step 2902 where it is determined if more than 10 seconds have passed since the last change in I Press 3P. If YES, step 2904 is executed to determine if Press 3P exceeds its minimum allowed value. If either of the conditions tested in steps 2902 or 2904 are not met, the NO branches are taken to step 2916. Following the YES branch from step 2904, step 2906 is executed to reduce Press 3P and reset of the appropriate timer. Processing then advances to step 2916.

Following the YES branch from step 2900, step 2907 is executed to reset timers running on Press 1, Press 2P and Press 3P. The timers track time elapsed since the last changes in value of Press 1, Press 2P and Press 3P. Step 2908 is then executed to determine if the time elapsed since the last boost of upper base pressure exceeds 5 seconds. If YES, step 2910 is executed to boost Press 3P by a unit and to reset the boost timer for Press 3P. Next, step 2912 is executed to determine if the new Press 3P exceeds its maximum allowed level. If YES, step 2913 is executed to boost base pressure Press I and to reduce Press 3P to its maximum permitted level. Next, step 2914 is executed to determine if Press I now exceeds the maximum permitted level for command pressure. If NO, processing advances to step 2916. If YES, step 2915 is interposed and executed to reset Press I to the maximum permitted value for command pressure. Following the NO branch from step 2908, step 2912 or from step 2914 advances processing to step 2916.

At step 2916, the sum of Press 1 and Press 3P are compared to the maximum permitted value for command pressure. Where the sum exceeds the maximum permitted value, the YES branch is taken to step 2918 to set Press 3 to the maximum permitted command pressure level less Press 1. Along the NO branch from step 2916 step 2920 determines if the inspiration flag is set. If YES, step 2922 is executed to set Press 3 to Press 3P. If NO, step 2924 is executed to set Press 3 to zero because expiration is occurring.

Following steps 2918, 2922, or 2924, processing advances to step 2926 where it is determined if Press 3 exceeds a minimum level. If Press 3 is greater than the minimum limit, pressure level Press 2 is reset to 0 and the subprocess exited. If Press 3 does not exceed the minimum level, the pressure components are left unchanged and the subprocess exited.

FIG. 29 is a logical flow chart illustrating adjustment of command pressure. The process is entered in step 3000 where command pressure is set equal to the sum of components Press 1, Press 2P and Press 3P. In step 3002 the phase of an oscillating pressure value is reversed, i.e. the negative of the old value is used. Next, step 3004 is executed to set output pressure to command pressure plus oscillating pressure. In step 3006 output pressure value is output to the digital to analog converter. Processing is then returned to the appropriate parent subroutine.

The invention provides air or a mixture of breathable gases at low pressure to a sleeper when sleep disorder breathing is not occurring. This is more comfortable to the user than the higher pressures used to control sleep disorder breathing. If the system fails to stop the sleep disorder breathing an alarm can be sounded to wake other people or the person to avoid a potentially dangerous situation. The system automatically adapts to the level of air pressure required by the user during the night.

While the invention has been shown in only one of its forms, it should be apparent to those skilled in the art that it is not so limited but is susceptible to various changes without departing from the scope of the invention.

What is claimed is:

1. A method of controlling sleep disorder breathing in a person, the method comprising the steps of:

connecting an interface from a source of compressed air to a person's breathing passages;

supplying compressed air from the source of compressed air through the interface to the person's breathing passages;

measuring flow related variables and pressure variables of the compressed air in the interface;

detecting from the measured flow related variables and the measured pressure variables indications of sleep disorder breathing by:

computing a standard deviation value for the measured flow related variables over an interval;

periodically determining if the computed standard deviation value exceeds a standard deviation threshold; and comparing the computed standard deviation value with the standard deviation threshold over a certain time interval to establish occurrence of pharyngeal wall vibration;

responsive to the detection of indications of sleep disorder breathing, adjusting pressure of the compressed air while continuing to monitor the measured flow related variables and the measured pressure variables for sleep disorder breathing; and responsive to passage of a period without detection of indications of sleep disorder breathing, adjusting pressure of the compressed air.

2. A method as set forth in claim 1, wherein the step of detecting indications of sleep disorder breathing includes:

computing a running mean of a series of the measured flow related variables;

setting a hypopnea threshold based on a fraction of the running mean for the measured flow related variables;

comparing a value determined over an interval of samples for the measured flow related variable against the hypopnea threshold for indication of sleep disorder breathing.

3. A method as set forth in claim 1, wherein the step of detecting indications of sleep disorder breathing includes:

computing a mean over an interval of the measured flow related variables; and comparing the mean from the computing step to an apnea threshold.

4. A method as set forth in claim 1, wherein the measured flow rate variables include a measurement of pressure difference along the interface and the step of detecting indications of sleep disorder breathing includes:

accumulating a plurality of mean pressure difference measurements;

accumulating a plurality of pressure measurements;

calculating energy values for the accumulated measurements of pressure differences and pressure;

determining a phase difference between the pressure measurements and the pressure difference measurements; and comparing the energy values and the phase difference to thresholds to determine full or partial closure of a patient's breathing passages.

5. A method as set forth in claim 1, wherein the step of detecting indication of sleep disorder breathing further includes:

determining if the measured flow related variable exceeds a threshold for an interface off condition;

responsive to an affirmative determination of the interface off condition, signaling the interface off condition;

absent determination of an interface off condition, determining if a pressure difference mean baseline exceeds a threshold for an interface leak condition; and responsive to an affirmative determination of an interface leak condition, signaling the interface leak condition.

6. A method as set forth in claim 1, wherein the step of detecting sleep disorder breathing further includes:

comparing a baseline calculation and a standard deviation calculation for a plurality of samples of measured pressure related variables against a plurality of a thresholds for failure of supply of compressed air.

7. A method as set forth in claim 1, wherein the step of detecting indication of sleep disorder breathing further includes:

determining if the measured flow related variable exceeds a threshold for an interface off condition;

responsive to an affirmative determination of the interface off condition, signaling the interface off condition;

absent determination of an interface off condition, determining if a pressure difference mean baseline exceeds a threshold for an interface leak condition; and responsive to an affirmative determination of an interface leak condition, signaling the interface leak condition.

8. A method for sleep disorder breathing therapy of a person, comprising the steps of:

connecting a face mask from an air compressor to a person's breathing passages;

supplying air from the air compressor through an interface to the face mask;

periodically measuring a pressure difference along the interface and a pressure in the face mask;

detecting from the measured pressure difference and the face mask pressure indications of sleep disorder breathing by:

taking pressure difference measurements at each of a plurality of sample points during an interval;

calculating a mean value for the sample points over each interval and a standard deviation for the sample of points over the interval;

generating an initial base line from an accumulation of mean values for a sequence of intervals of sample point;

thereafter adjusting the baseline for each subsequent pressure difference mean calculated;

generating an area of respiration value from the area difference between the base line and calculated mean values;

maintaining a first-in, first-out list of areas of respiration values for a plurality of respiration measurements;

calculating a hypopnea threshold from the values in the first-in, first-out list;

comparing each area of respiration value with the hypopnea threshold and indicating hypopnea if the area of respiration value fails to meet the threshold either as a single value or multiple values over a period of time;

responsive to the detection of indications of sleep disorder breathing, adjusting pressure from the compressor while continuing to measure the pressure and the pressure difference for continued indication of sleep disorder breathing; and responsive to passage of a period without detection of indications of sleep disorder breathing, adjusting pressure of the compressed air.

9. A method as set forth in claim 8, wherein the step of detecting indications of sleep disorder breathing further includes:

providing an apnea threshold;

comparing the absolute value of the difference between the mean pressure difference for a latest interval and the baseline against the apnea threshold; and if the absolute value is less than the apnea threshold over a period of time, signaling that apnea is occurring.

10. A method as set forth in claim 8, wherein the step of supplying air from the air compressor through the interface to a face mask further includes:

setting an initial command pressure to control pressure from the air compressor at a minimum setting.

11. A method as set forth in claim 10, wherein the step of adjusting pressure from the compressor while continuing to monitor pressure and pressure difference for continued indication of sleep disorder breathing further includes:

adjusting command pressure in response to signaling by the step of detecting, indications of sleep disorder breathing.

12. A method as set forth in claim 11, wherein the step of detecting indications of sleep disorder breathing further include:

setting a pharyngeal wall vibration threshold;

comparing variation of the standard deviation for a most current interval beyond a standard deviation threshold against the pharyngeal wall vibration threshold; and responsive to the variation in standard deviation exceeding the threshold over a period of time and signaling the occurrence of pharyngeal wall vibration.

13. A method as set forth in claim 8, wherein the step of adjusting pressure further includes:

responsive to determination that indications of sleep disorder breathing are present, periodically boosting the pressure for as long as the indications remain and pressure is less than a maximum permitted level; and absent determination that indications of sleep disorder breathing are present, periodically reducing the pressure as long as pressure remains above a minimum permitted level.

14. Apparatus for controlling sleep disorder breathing comprising:

a source of compressed breathable gas;

an interface having a first and a second end, the first end connected to the source of compressed breathable gas and the second end adapted to fit over a person's breathing passages;

means for measuring differential pressure from the first end to the second end of the interface;

means for measuring pressure in the second end of the interface;

means for detecting indications in the measurements of sleep disorder breathing from the measurement of pressure and differential pressure, including:

means for calculating a mean over a set of sample points taken during an interval and for calculating a standard deviation for the set of sample points;

means for accumulating mean values for a plurality of intervals;

means for generating an initial base line from the accumulation of mean values for a sequence of intervals of sample points;

means for adjusting the initial baseline for each subsequent pressure difference mean calculated;

means for generating an area of respiration value from the area difference between the base line and each pressure difference mean calculated;

means for maintaining a first-in, first-out list of areas of respiration values for a plurality of respiration measurements;

means for calculating a hypopnea threshold from the measurements in the first-in, first-out list;

means for comparing each area of respiration value against the hypopnea threshold and for indicating hypopnea if the area fails to meet the threshold either as a single value or multiple values over a period of time;

means responsive to detection of indications of sleep disorder breathing for adjusting pressure of breathable gas from the source of breathable gas; and means responsive to passage of a period of time without detection of indication of sleep disorder breathing for adjusting pressure from the source of breathable gas.

15. Apparatus as set forth in claim 14, wherein the means for detecting indications of sleep disorder breathing further include:

an apnea threshold;

means for comparing the absolute value of the difference between the mean pressure difference for a latest interval and the baseline against the apnea threshold; and means responsive to the absolute value being less than the apnea threshold over a period of time for signaling that apnea is occurring.

16. Apparatus as set forth in claim 14, wherein the means for supplying breathable gas to the interface further include:

means for setting an initial command pressure to control pressure from the compressed breathable gas source at a minimum setting.

17. Apparatus as set forth in claim 16, wherein the means for adjusting pressure from the compressed breathable gas source while continuing to monitor pressure and pressure difference for continued indication of sleep disorder breathing further include:

means for adjusting command pressure in response to signaling by the means for detecting of sleep disorder breathing.

18. Apparatus as set forth in claim 17, wherein the means for detecting indications of sleep disorder breathing further include:

means for setting a minimum standard function of the command pressure;

means for computing the area and duration of the standard deviation curve above the minimum standard deviation threshold;

means for comparing the area and duration against their corresponding thresholds; and means responsive to the area and duration exceeding their respective thresholds for signaling occurrence of pharyngeal wall vibration.

19. Apparatus as set forth in claim 14, wherein the means for adjusting pressure further include:

means responsive to determination that an indication of sleep disorder breathing is present for periodically boosting pressure from the source of compressed breathable gas for as long as the indication remains and pressure is less than a maximum permitted level; and means responsive to passage of a period without determination that indications of sleep disorder breathing are present for periodically reducing pressure as long as pressure remains above a minimum permitted level.

20. A method of diagnosis of sleep disorder breathing, comprising the steps of:

forcing air through a pressure line to a person's breathing passages;

periodically sampling a pressure rate variable related to pressure of air in the pressure line;

accumulating samples of the pressure rate variable;

generating a mean pressure rate for intervals of samples of the pressure rate variable;

generating a variance measure for the intervals of samples of the pressure rate variable;

comparing the variance measure with a threshold to detect pharyngeal wall vibration;

maintaining a running average of mean pressure rates;

comparing a generated mean pressure rate against the running average to detect hypopnea or apnea in the patient and signaling the results of the comparing steps where sleep disorder breathing is detected;

calculating a hypopnea threshold from the running average of the mean pressure rates;

following detection of hypopnea or apnea in the step of comparing the generated mean pressure rate against the running average, comparing the generated mean pressure rate to the hypopnea threshold;

applying a secondary oscillating component to the forced air in the flow line;

periodically sampling pressure at multiple points in the flow line;

accumulating samples of pressure;

utilizing the samples of pressure to detect full, partial, or no obstruction of the patient's breathing passage;

in the step of signaling sleep disorder breathing, where hypopnea but not apnea is detected and no obstruction of the patient's nostril passages is detected, signaling central sleep hypopnea;

in the step of signaling sleep disorder breathing, where apnea is detected in the hypopnea threshold comparison step and no obstruction of the patient's breathing passages is detected, signaling central sleep apnea;

in the step of signaling sleep disorder breathing, where hypopnea is detected, but not apnea, and an obstruction of the patient's breathing passages is detected, signaling obstructive sleep hypopnea; and in the step of signaling sleep disorder breathing, where apnea is detected and an obstruction of the patient's breathing passages is detected, signaling obstructive sleep apnea;

responsive to detection of obstructive sleep hypopnea, adjusting pressure of forced air during inhalation by the patient and reducing pressure of forced air during exhalation if above a minimum;

responsive to detection of obstructive sleep apnea, increasing pressure of forced air during inhalation and exhalation; and absent detection of sleep disorder breathing, adjusting pressure of forced air during inhalation and exhalation to the minimum.

21. A method as set forth in claim 20, and further comprising:

responsive to detection of pharyngeal wall vibration, adjusting the pressure of forced air;

responsive to detection of central sleep hypopnea, increasing pressure of forced air during inhalation and reducing pressure of forced air during exhalation; and responsive to detection of central sleep apnea, increasing pressure of forced air during inhalation and reducing pressure of forced air during exhalation.

22. A method of controlling sleep disorder breathing in a person, the method comprising the steps of:

connecting an interface from a source of compressed air to a person's breathing passages;

supplying compressed air from the source of compressed air through the interface to the person's breathing passages;

continuously measuring flow related variables and pressure variables of the compressed air in the interface by computing a standard deviation value for the measured flow related variables over an interval;

continuously generating at least one standard deviation threshold value from the measured flow related variables and measured pressure variables, wherein the standard deviation threshold value is adapted to changing conditions occurring in at least the person's breathing passages;

comparing the measured flow related variables and measured pressure variables to the standard deviation threshold value to detect indications of sleep disorder breathing from the measured flow related variables and the measured pressure variables by periodically determining if the computed standard deviation value exceeds the standard deviation threshold value and comparing the computed standard deviation value with the standard deviation threshold value over a certain time interval to establish occurrence of pharyngeal wall vibration;

responsive to the detection of indications of sleep disorder breathing, adjusting pressure of the compressed air while continuing to measure the measured flow related variables and the measured pressure variables for sleep disorder breathing; and responsive to passage of a period without detection of indications of sleep disorder breathing, adjusting pressure of the compressed air.

23. A method as set forth in claim 22, wherein the steps of generating the threshold and comparing the measured flow related variables and measured pressure related variables further includes:

computing a running mean of a series of measured flow related variables;

setting a hypopnea threshold based on a fraction of the running mean for the measured flow related variables; and comparing a value determined over an interval of samples for the measured flow related variable against the hypopnea threshold for indication of sleep disorder breathing.

24. A method as set forth in claim 22, wherein the steps of generating the threshold and comparing the measured flow related variables and measured pressure related variables further includes:

computing a mean over an interval of measured flow related variables; and comparing the mean from the computing step to an apnea threshold.

25. A method as set forth in claim 22, wherein the steps of generating the threshold and comparing the measured flow related variables and measured pressure related variables further includes:

determining if the measured flow related variable exceeds a threshold for an interface off condition;

responsive to an affirmative determination of the interface off condition, signaling the interface off condition;

absent determination of an interface off condition, determining if a pressure difference mean baseline exceeds a threshold for an interface leak condition; and responsive to an affirmative determination of an interface leak condition, signaling the interface leak condition.

26. A method as set forth in claim 22, wherein the steps of generating the threshold and comparing the measured flow related variables and measured pressure related variables further includes:

comparing a baseline calculation and a standard deviation calculation for a plurality of samples of measured pressure related variables against a plurality of a thresholds for failure of supply of compressed air.

27. Apparatus for controlling sleep disorder breathing comprising:

a source of compressed breathable gas;

means for setting an initial command pressure to control pressure from the compressed breathable gas source at a minimum setting;

an interface having a first end and a second end, the first end connected to the source of compressed breathable gas and the second end adapted to fit over a person's breathing passages;

means for measuring differential pressure from the first end to the second end of the interface;

means for measuring pressure in the second end of the interface;

means for detecting indications in the measurements of sleep disorder breathing from the measurement of pressure and differential pressure, including:
 means for setting a minimum standard deviation threshold as a function of the command pressure;
 means for computing the area and duration of the standard deviation curve above the minimum standard deviation threshold; means for comparing the area and duration against their corresponding thresholds;
 means responsive to the area and duration exceeding their respective thresholds for signaling occurrence of pharyngeal wall vibration;

means responsive to detection of indications of sleep disorder breathing for adjusting pressure of breathable gas from the source of breathable gas; and means responsive to passage of a period of time without detection of indication of sleep disorder breathing for adjusting pressure from the source of breathable gas.

28. Apparatus as set forth in claim 27, wherein the means for detecting indications of sleep disorder breathing further include:

means for applying a secondary oscillating component to the breathable gas;

means for accumulating a plurality of mean pressure difference measurements;

means for accumulating a plurality of pressure measurements;

means for calculating energy values for the accumulated measurements of pressure differences and pressure;

means for determining a phase difference between the pressure measurements and the pressure difference measurements;

means for comparing the energy values and the phase difference to thresholds to determine full or partial closure of a patient's breathing passages;

means responsive to detection of indications of sleep disorder breathing for adjusting pressure of breathable gas from the source of breathable gas; and means responsive to passage of a period of time without detection of indication of sleep disorder breathing for adjusting pressure from the source of breathable gas.

29. Apparatus as set forth in claim 27, wherein the means for detecting indications of sleep disorder breathing further include:

means for calculating a mean over a set of sample points taken during an interval and for calculating a standard deviation for the set of sample points;

means for accumulating mean values for a plurality of intervals;

means for generating an initial base line from the accumulation of mean values for a sequence of intervals of sample points;

means for adjusting the initial baseline for each subsequent pressure difference mean calculated;

means for generating an area of respiration value from the area difference between the base line and each pressure difference mean calculated;

means for maintaining a first-in, first-out list of areas of respiration values for a plurality of respiration measurements;

means for calculating a hypopnea threshold from the measurements in the first-in, first-out list; and means for comparing each area of respiration value against the hypopnea threshold and for indicating hypopnea if the area fails to meet the threshold either as a single value or multiple values over a period of time.

30. Apparatus as set forth in claim 27, wherein the means for detecting indications of sleep disorder breathing further include:

an apnea threshold;

means for comparing the absolute value of the difference between the mean pressure difference for a latest interval and the baseline against the apnea threshold; and means responsive to the absolute value being less than the apnea threshold over a period of time for signaling that apnea is occurring.

31. Apparatus as set forth in claim 27, wherein the means for adjusting pressure further include:

means responsive to determination that an indication of sleep disorder breathing is present for periodically boosting pressure from the source of compressed breathable gas for as long as the indication remains and pressure is less than a maximum permitted level; and means responsive to passage of a period without determination that indications of sleep disorder breathing are present for periodically reducing pressure as long as pressure remains above a minimum permitted level.

32. Apparatus as set forth in claim 27, wherein the means for adjusting pressure from the compressed breathable gas source while continuing to monitor pressure and pressure difference for continued indication of sleep disorder breathing further include:

means for adjusting command pressure in response to signaling by the means for detecting of sleep disorder breathing.

33. Apparatus for controlling sleep disorder breathing comprising:

a source of compressed breathable gas;

means for applying a secondary oscillating component to the breathable gas;

an interface connected at a first end to the source of compressed breathable gas and adapted at a second end fit over a person's breathing passages;

means for measuring differential pressure from the first end to the second end of the interface;

means for measuring pressure in the second end of the interface;

means for detecting indications in the measurements of sleep disorder breathing from the measurement of pressure and differential pressure, including:

means for accumulating a plurality of mean pressure difference measurements;

means for accumulating a plurality of pressure measurements;

means for calculating energy values for the accumulated measurements of pressure differences and pressure;

means for determining a phase difference between the pressure measurements and the pressure difference measurements;

means for comparing the energy values and the phase difference to thresholds to determine full or partial closure of a patient's breathing passages;

means responsive to detection of indications of sleep disorder breathing for adjusting pressure of breathable gas from the source of breathable gas; and means responsive to passage of a period of time without detection of indication of sleep disorder breathing for adjusting pressure from the source of breathable gas.

34. Apparatus as set forth in claim 33, wherein the means for detecting indications of sleep disorder breathing further include:

means for calculating a mean over a set of sample points taken during an interval and for calculating a standard deviation for the set of sample points;

means for accumulating mean values for a plurality of intervals;

means for generating an initial base line from the accumulation of mean values for a sequence of intervals of sample points;

means for adjusting the initial baseline for each subsequent pressure difference mean calculated;

means for generating an area of respiration value from the area difference between the base line and each pressure difference mean calculated;

means for maintaining a first-in, first-out list of areas of respiration values for a plurality of respiration measurements;

means for calculating a hypopnea threshold from the measurements in the first-in, first-out list; and means for comparing each area of respiration value against the hypopnea threshold and for indicating hypopnea if the area fails to meet the threshold either as a single value or multiple values over a period of time.

35. Apparatus as set forth in claim 33, wherein the means for detecting indications of sleep disorder breathing further include:

an apnea threshold;

means for comparing the absolute value of the difference between the mean pressure difference for a latest interval and the baseline against the apnea threshold; and means responsive to the absolute value being less than the apnea threshold over a period of time for signaling that apnea is occurring.

36. Apparatus as set forth in claim 33, wherein the means for detecting indications of sleep disorder breathing further include:

means for setting a minimum standard deviation threshold as a function of the command pressure;

means for computing the area and duration of the standard deviation curve above the minimum standard deviation threshold;

means for comparing the area and duration against their corresponding thresholds; and means responsive to the area and duration exceeding their respective thresholds for signaling occurrence of pharyngeal wall vibration.

37. Apparatus as set forth in claim 33, wherein the means for adjusting pressure further include:

means responsive to determination that an indication of sleep disorder breathing is present for periodically boosting pressure from the source of compressed breathable gas for as long as the indication remains and pressure is less than a maximum permitted level; and means responsive to passage of a period without determination that indications of sleep disorder breathing are present for periodically reducing pressure as long as pressure remains above a minimum permitted level.

38. Apparatus as set forth in claim 33, wherein the means for adjusting pressure from the compressed breathable gas source while continuing to monitor pressure and pressure difference for continued indication of sleep disorder breathing further include:

means for adjusting command pressure in response to signaling by the means for detecting of sleep disorder breathing.

39. A method of controlling sleep disorder breathing in a person, the method comprising the steps of:

connecting an interface from a source of compressed air to a person's breathing passages;

supplying compressed air from the source of compressed air through the interface to the person's breathing passages;

measuring flow related variables and pressure variables of the compressed air in the interface;

detecting from the measured flow related variables and the measured pressure variables indications of sleep disorder breathing by:

applying a secondary oscillating component to the compressed air;

accumulating a plurality of mean pressure difference measurements;

accumulating a plurality of pressure measurements;

calculating energy values for the accumulated measurements of pressure differences and pressure;

determining a phase difference between the pressure measurements and the pressure difference measurements;

comparing the energy values and the phase difference to thresholds to determine full or partial closure of a patient's breathing passages;

responsive to the detection of indications of sleep disorder breathing, adjusting pressure of the compressed air while continuing to monitor the measured flow related variables and the measured pressure variables for sleep disorder breathing; and responsive to passage of a period without detection of indications of sleep disorder breathing, adjusting pressure of the compressed air.

40. A method as set forth in claim 39, wherein the step of detecting indications of sleep disorder breathing includes:

computing a running mean of a series of the measured flow related variables;

setting a hypopnea threshold based on a fraction of the running mean for the measured flow related variables;

comparing a value determined over an interval of samples for the measured flow related variable against the hypopnea threshold for indication of sleep disorder breathing.

41. A method as set forth in claim 39, wherein the step of detecting indications of sleep disorder breathing includes:

computing a mean over an interval of the measured flow related variables; and comparing the mean from the computing step to an apnea threshold.

42. A method as set forth in claim 39, wherein the measured flow rate variables include a measurement of pressure difference along the interface and the step of detecting indications of sleep disorder breathing includes:

computing a standard deviation value for the measured flow related variables over an interval;

periodically determining if the computed standard deviation value exceeds a standard deviation threshold; and comparing the computed standard deviation value with the standard deviation threshold over a certain time interval to establish occurrence of pharyngeal wall vibration.

43. A method as set forth in claim 39, wherein the step of detecting sleep disorder breathing further includes:

comparing a baseline calculation and a standard deviation calculation for a plurality of samples of measured pressure related variables against a plurality of a thresholds for failure of supply of compressed air.

* * * * *